(12) United States Patent
Franz et al.

(10) Patent No.: US 6,555,581 B1
(45) Date of Patent: Apr. 29, 2003

(54) LEVOTHYROXINE COMPOSITIONS AND METHODS

(75) Inventors: G. Andrew Franz, St. Louis, MO (US); Elaine A. Strauss, Seminole, FL (US); Philip A. DiMenna, St. Petersburg, FL (US); Rocco L. Gemma, Dover, OH (US)

(73) Assignee: Jones Pharma, Inc., St. Petersburg, FL (US)

( * ) Notice: Subject to any disclaimer, the term of this patent is extended or adjusted under 35 U.S.C. 154(b) by 0 days.

(21) Appl. No.: 10/077,677

(22) Filed: Feb. 15, 2002

Related U.S. Application Data

(60) Provisional application No. 60/269,009, filed on Feb. 15, 2001, provisional application No. 60/268,998, filed on Feb. 15, 2001, provisional application No. 60/311,523, filed on Aug. 10, 2001, provisional application No. 60/311,552, filed on Aug. 10, 2001, provisional application No. 60/311,549, filed on Aug. 10, 2001, provisional application No. 60/311,522, filed on Aug. 10, 2001, provisional application No. 60/311,524, filed on Aug. 10, 2001, provisional application No. 60/311,550, filed on Aug. 10, 2001, provisional application No. 60/311,525, filed on Aug. 10, 2001, provisional application No. 60/312,114, filed on Aug. 14, 2001, provisional application No. 60/312,113, filed on Aug. 14, 2001, provisional application No. 60/312,287, filed on Aug. 14, 2001, provisional application No. 60/312,184, filed on Aug. 14, 2001, provisional application No. 60/312,273, filed on Aug. 14, 2001, provisional application No. 60/312,206, filed on Aug. 14, 2001, provisional application No. 60/312,289, filed on Aug. 14, 2001, provisional application No. 60/312,483, filed on Aug. 14, 2001, provisional application No. 60/344,764, filed on Oct. 29, 2001, provisional application No. 60/344,763, filed on Oct. 29, 2001, provisional application No. 60/347,828, filed on Oct. 29, 2001, provisional application No. 60/345,344, filed on Oct. 29, 2001, provisional application No. 60/345,343, filed on Oct. 29, 2001, provisional application No. 60/344,762, filed on Oct. 29, 2001, provisional application No. 60/344,744, filed on Oct. 29, 2001, and provisional application No. 60/347,827, filed on Oct. 29, 2001.

(51) Int. Cl.$^7$ .............................. A61K 9/20; A61K 9/14; A61K 9/48; A61K 31/195; A61K 47/38

(52) U.S. Cl. .................... 514/567; 514/492; 514/781; 514/951; 514/952; 514/960; 514/961; 514/962; 514/970; 424/451; 424/452; 424/464; 424/465; 424/466; 424/474; 424/480; 424/489; 424/490; 424/494

(58) Field of Search ........................... 514/567, 492, 514/781, 951, 952, 960, 961, 962, 970; 424/451, 452, 464–466, 474, 480, 489, 490, 494

(56) References Cited

U.S. PATENT DOCUMENTS

| | | |
|---|---|---|
| 2,426,643 A | 9/1947 | Ridgway |
| 2,436,005 A | 2/1948 | Hopps et al. |
| 2,579,668 A | 12/1951 | Hems et al. |
| 2,642,426 A | 6/1953 | West et al. |
| 2,705,726 A | 4/1955 | Sydney |
| 2,802,869 A | 8/1957 | Montgomery |
| 2,823,164 A | 2/1958 | Pitt-Rivers et al. |
| 2,866,738 A | 12/1958 | Pasquale et al. |
| 2,993,928 A | 7/1961 | Razdan et al. |
| 3,035,974 A | 5/1962 | Israel et al. |
| 3,380,818 A | 4/1968 | Smith |
| 3,452,599 A | 7/1969 | Kishel |
| 3,666,854 A | 5/1972 | Eisentraut et al. |
| 3,808,332 A | 4/1974 | Reynolds et al. |
| 3,826,767 A | 7/1974 | Hoover et al. |
| 4,015,939 A | 4/1977 | Lewin et al. |
| 4,110,470 A | 8/1978 | Kummer et al. |
| 4,115,537 A | 9/1978 | Driscoll et al. |

(List continued on next page.)

FOREIGN PATENT DOCUMENTS

| | | |
|---|---|---|
| DE | 4318577 | 12/1994 |
| DE | 19541128 | 10/1995 |
| DE | 19830246 | 1/2000 |
| EP | 0202051 | 11/1986 |
| EP | 248548 | 12/1987 |
| EP | 255404 | 2/1988 |
| EP | 256878 | 2/1988 |
| EP | 259157 | 3/1988 |
| EP | 268912 | 6/1988 |
| EP | 271204 | 6/1988 |
| EP | 278908 | 8/1988 |
| EP | 287189 | 10/1988 |

(List continued on next page.)

OTHER PUBLICATIONS

Novelty Computer Search for levothyroxine and Microcrystalline Cellulose, pp. 4–129 (2002).

De Meijer, P.J.J.: Analysis of Thyroid and Thyroxin by Means of High performance Liquid Chromatography, *Pharmaceutisch Weekblad*, 116:1085–1089 (1981).

Ceolus™ Microcrystalline Cellulose, NF, Ph.. Eur., JP For Smaller Tablets, FMC, pp. 1–6 (Oct. 1997).

Avicel PH Microcrystalline Cellulose, NF, Ph., Eur., JP, BP A World of Difference, FMC BioPolymer, pp. 1–11 (Oct. 1998).

Food and Drug Administration Notice Regarding Levothyroxine Sodium, Department of Helath and Human Sciences, Food and Drug Administration, Federal Register, 62(157):1–12 (Aug. 14, 1997).

Jerome Stevens Pharmaceuticals, Inc., Petition to FDA, pp. 1–129 (Mar. 28, 2002) (File Copy).

Surface Profile Parameters, Surface Meterology Guide—Profile Parameters, pp. 1–23 (Jan. 30, 2001).

(List continued on next page.)

*Primary Examiner*—John Pak
(74) *Attorney, Agent, or Firm*—Edwards & Angell, LLP; Peter Manso, Esq.

(57) ABSTRACT

The present invention generally relates to stable pharmaceutical compositions, and methods of making and administering such compositions. In one aspect, the invention features stabilized pharmaceutical compositions that include pharmaceutically active ingredients such as levothyroxine (T4) sodium and liothyronine (T3) sodium (thyroid hormone drugs), preferably in an immediate release solid dosage form. Also provided are methods for making and using such immediate release and stabilized compositions.

25 Claims, 4 Drawing Sheets

U.S. PATENT DOCUMENTS

| | | |
|---|---|---|
| 4,288,546 A | 9/1981 | Narasimhan et al. |
| 4,344,934 A | 8/1982 | Martin et al. ............... 514/462 |
| 4,369,172 A | 1/1983 | Schor et al. |
| 4,479,947 A | 10/1984 | Christensen et al. |
| 4,539,198 A | 9/1985 | Powell et al. ............... 424/464 |
| 4,585,652 A | 4/1986 | Miller et al. |
| 4,587,258 A | 5/1986 | Gold et al. |
| 4,615,697 A | 10/1986 | Robinson et al. |
| 4,654,331 A | 3/1987 | Christensen et al. |
| 4,666,703 A | 5/1987 | Kopf |
| 4,690,824 A | 9/1987 | Powell et al. ............... 424/468 |
| 4,705,692 A | 11/1987 | Tanaka et al. |
| 4,795,436 A | 1/1989 | Robinson et al. |
| 4,795,644 A | 1/1989 | Zentner et al. |
| 4,814,183 A | 3/1989 | Zentner et al. |
| 4,818,531 A | 4/1989 | Anderson et al. |
| 4,851,228 A | 7/1989 | Zentner et al. |
| 4,877,774 A | 10/1989 | Pitha et al. |
| 4,960,690 A | 10/1990 | Ellis et al. |
| 4,973,469 A | 11/1990 | Mulligan et al. ........... 424/461 |
| 4,980,358 A | 12/1990 | Smith et al. |
| 4,983,392 A | 1/1991 | Robinson et al. |
| 5,001,115 A | 3/1991 | Sloan et al. |
| 5,061,722 A | 10/1991 | Teetz et al. |
| 5,064,823 A | 11/1991 | Lee et al. |
| 5,073,379 A | 12/1991 | Klimesch et al. |
| 5,073,555 A | 12/1991 | Smith et al. |
| 5,099,001 A | 3/1992 | Scarano et al. |
| 5,158,978 A | 10/1992 | Rubin et al. |
| 5,176,953 A | 1/1993 | Jacoby et al. |
| 5,225,196 A | 7/1993 | Robinson |
| 5,225,204 A | 7/1993 | Chen et al. |
| 5,244,786 A | 9/1993 | Picone et al. |
| 5,310,912 A | 5/1994 | Neumeyer et al. |
| 5,317,035 A | 5/1994 | Jacoby et al. |
| 5,324,522 A | 6/1994 | Krenning et al. |
| 5,412,005 A | 5/1995 | Bastioli et al. |
| 5,439,666 A | 8/1995 | Neumeyer et al. |
| 5,449,522 A | 9/1995 | Hill et al. |
| 5,461,140 A | 10/1995 | Heller et al. |
| 5,574,150 A | 11/1996 | Yaginuma et al. ............. 536/56 |
| 5,594,070 A | 1/1997 | Jacoby et al. |
| 5,607,691 A | 3/1997 | Hale et al. |
| 5,618,338 A | 4/1997 | Kurabayashi et al. |
| 5,624,612 A | 4/1997 | Sewall et al. |
| 5,635,209 A | 6/1997 | Groenewoud et al. |
| 5,648,096 A | 7/1997 | Gander et al. |
| 5,656,286 A | 8/1997 | Miranda et al. |
| 5,670,380 A | 9/1997 | Wu |
| 5,686,094 A | 11/1997 | Acharya |
| 5,698,179 A | 12/1997 | Neumeyer et al. |
| 5,718,969 A | 2/1998 | Sewall et al. |
| 5,728,810 A | 3/1998 | Lewis et al. |
| 5,738,984 A | 4/1998 | Shoseyov et al. |
| 5,750,089 A | 5/1998 | Neumeyer et al. |
| 5,753,254 A | 5/1998 | Khan et al. |
| 5,767,227 A | 6/1998 | Latham et al. |
| 5,784,992 A | 7/1998 | Petitte et al. |
| 5,800,836 A | 9/1998 | Morella et al. |
| 5,811,547 A | 9/1998 | Nakamichi et al. |
| 5,856,359 A | 1/1999 | Fischer et al. |
| 5,888,774 A | 3/1999 | Delcuve |
| 5,897,910 A | 4/1999 | Rosenberg et al. |
| 5,910,569 A | 6/1999 | Latham et al. |
| 5,916,910 A | 6/1999 | Lai |
| 5,939,099 A | 8/1999 | Grabowski et al. |
| 5,945,127 A | 8/1999 | Breitenbach et al. |
| 5,952,451 A | 9/1999 | Zhao |
| 5,955,105 A | 9/1999 | Mitra et al. |
| 5,958,453 A | 9/1999 | Ohno et al. |
| 5,958,979 A | 9/1999 | Lahr et al. |
| 5,985,607 A | 11/1999 | Delcuve et al. |
| 5,989,894 A | 11/1999 | Lewis et al. |
| 6,001,391 A | 12/1999 | Zeidler et al. |
| 6,008,318 A | 12/1999 | Zhao et al. |
| 6,009,690 A | 1/2000 | Rosenberg et al. |
| 6,024,976 A | 2/2000 | Miranda et al. |
| 6,030,613 A | 2/2000 | Blumberg et al. |
| 6,046,177 A | 4/2000 | Stella et al. |
| 6,051,253 A | 4/2000 | Zettler et al. |
| 6,056,975 A | 5/2000 | Mitra et al. |
| 6,080,383 A | 6/2000 | Rose et al. |
| 6,080,426 A | 6/2000 | Amey et al. |
| 6,110,909 A | 8/2000 | Yukimasa et al. |
| 6,117,911 A | 9/2000 | Grainger et al. |
| 6,120,802 A | 9/2000 | Breitenbach et al. |
| 6,132,659 A | 10/2000 | Rosenberg et al. |
| 6,143,717 A | 11/2000 | Hill et al. |
| 6,150,424 A | 11/2000 | Breitenbach et al. |
| 6,153,223 A | 11/2000 | Apelian et al. |
| 6,183,596 B1 | 2/2001 | Matsuda et al. |
| 6,187,342 B1 | 2/2001 | Zeidler et al. |
| 6,190,591 B1 | 2/2001 | van Lengerich |
| 6,190,696 B1 | 2/2001 | Groenewoud et al. |
| 6,200,958 B1 | 3/2001 | Odaka et al. |
| 6,214,163 B1 | 4/2001 | Matsuda et al. |
| 6,221,383 B1 | 4/2001 | Miranda et al. |
| 6,221,402 B1 | 4/2001 | Itoh et al. |
| 6,245,350 B1 | 6/2001 | Amey et al. |
| 6,248,357 B1 | 6/2001 | Ohno et al. |
| 6,261,537 B1 | 7/2001 | Klaveness et al. |
| 6,268,197 B1 | 7/2001 | Schulein et al. |
| 6,284,271 B1 | 9/2001 | Lundberg et al. |
| 6,284,803 B1 | 9/2001 | Kothrade et al. |
| 6,290,990 B1 | 9/2001 | Grabowski et al. |
| 6,299,904 B1 | 10/2001 | Shimizu et al. |
| 6,323,236 B2 | 11/2001 | McElroy |
| 6,328,979 B1 | 12/2001 | Yamashita et al. |
| 6,328,994 B1 | 12/2001 | Shimizu et al. |
| 6,331,316 B1 | 12/2001 | Ullah et al. |
| 6,340,471 B1 | 1/2002 | Kershman et al. |
| 6,350,398 B1 | 2/2002 | Breitenbach et al. |
| 6,372,255 B1 | 4/2002 | Saslawski et al. |
| 6,383,471 B1 | 5/2002 | Chen et al. |
| 6,395,300 B1 | 5/2002 | Straub et al. |
| 6,399,101 B1 | 6/2002 | Frontanes et al. |
| 6,403,675 B1 | 6/2002 | Dang et al. |
| 6,406,297 B1 | 6/2002 | Raymond et al. |
| 6,410,587 B1 | 6/2002 | Grainger et al. |
| 6,414,126 B1 | 7/2002 | Ellsworth et al. |
| 6,423,256 B1 | 7/2002 | Kothrade et al. |
| 6,458,842 B1 | 10/2002 | Dickinson et al. |
| 6,468,503 B2 | 10/2002 | Rose et al. |
| 6,471,734 B1 | 10/2002 | Yeckley et al. |
| 6,485,726 B1 | 11/2002 | Blumberg et al. |
| 6,488,961 B1 | 12/2002 | Robinson et al. |
| 6,491,946 B1 | 12/2002 | Schreder et al. |
| 6,495,740 B1 | 12/2002 | Arioli et al. |
| 6,499,984 B1 | 12/2002 | Ghebre-Sellassie et al. |
| 6,500,658 B1 | 12/2002 | Wu et al. |

FOREIGN PATENT DOCUMENTS

| | | |
|---|---|---|
| EP | 295742 | 12/1988 |
| EP | 297290 | 1/1989 |
| EP | 297292 | 1/1989 |
| EP | 299533 | 1/1989 |
| EP | 300676 | 1/1989 |
| EP | 304156 | 2/1989 |
| EP | 307152 | 3/1989 |
| EP | 307970 | 3/1989 |
| EP | 310179 | 4/1989 |

| | | | | | |
|---|---|---|---|---|---|
| EP | 312157 | 4/1989 | EP | 705607 | 4/1996 |
| EP | 313515 | 4/1989 | EP | 707848 | 4/1996 |
| EP | 317070 | 5/1989 | EP | 381719 | 9/1996 |
| EP | 327918 | 8/1989 | EP | 471794 | 10/1996 |
| EP | 328106 | 8/1989 | EP | 737742 | 10/1996 |
| EP | 354322 | 2/1990 | EP | 741188 | 11/1996 |
| EP | 360006 | 3/1990 | EP | 742228 | 11/1996 |
| EP | 360258 | 3/1990 | EP | 754464 | 1/1997 |
| EP | 367463 | 5/1990 | EP | 759441 | 2/1997 |
| EP | 371683 | 6/1990 | EP | 482080 | 3/1997 |
| EP | 384522 | 8/1990 | EP | 620809 | 3/1997 |
| EP | 396282 | 11/1990 | EP | 761219 | 3/1997 |
| EP | 410411 | 1/1991 | EP | 761220 | 3/1997 |
| EP | 234708 | 2/1991 | EP | 769300 | 4/1997 |
| EP | 417721 | 3/1991 | EP | 770606 | 5/1997 |
| EP | 417840 | 3/1991 | EP | 696283 | 9/1997 |
| EP | 418596 | 3/1991 | EP | 796849 | 9/1997 |
| EP | 422699 | 4/1991 | EP | 532533 | 10/1997 |
| EP | 212603 | 6/1991 | EP | 812195 | 12/1997 |
| EP | 430190 | 6/1991 | EP | 482071 | 1/1998 |
| EP | 433043 | 6/1991 | EP | 823437 | 2/1998 |
| EP | 437367 | 7/1991 | EP | 834507 | 4/1998 |
| EP | 212599 | 10/1991 | EP | 839526 | 5/1998 |
| EP | 452862 | 10/1991 | EP | 578728 | 7/1998 |
| EP | 455042 | 11/1991 | EP | 862562 | 9/1998 |
| EP | 459226 | 12/1991 | EP | 870826 | 10/1998 |
| EP | 137280 | 3/1992 | EP | 890360 | 1/1999 |
| EP | 201071 | 3/1992 | EP | 895988 | 2/1999 |
| EP | 475148 | 3/1992 | EP | 773951 | 3/1999 |
| EP | 476645 | 3/1992 | EP | 905129 | 3/1999 |
| EP | 476646 | 3/1992 | EP | 625164 | 4/1999 |
| EP | 476658 | 3/1992 | EP | 907364 | 4/1999 |
| EP | 477286 | 4/1992 | EP | 753003 | 6/1999 |
| EP | 477827 | 4/1992 | EP | 919620 | 6/1999 |
| EP | 484785 | 5/1992 | EP | 921194 | 6/1999 |
| EP | 487774 | 6/1992 | EP | 945443 | 9/1999 |
| EP | 506211 | 9/1992 | EP | 952148 | 10/1999 |
| EP | 510662 | 10/1992 | EP | 654038 | 11/1999 |
| EP | 518587 | 12/1992 | EP | 957091 | 11/1999 |
| EP | 271974 | 3/1993 | EP | 962466 | 12/1999 |
| EP | 532611 | 3/1993 | EP | 962530 | 12/1999 |
| EP | 1 161 946 A2 | 3/1993 | EP | 817792 | 3/2000 |
| EP | 239306 | 6/1993 | EP | 984063 | 3/2000 |
| EP | 0 550 108 A1 | 7/1993 | EP | 990703 | 4/2000 |
| EP | 556395 | 8/1993 | EP | 995759 | 4/2000 |
| EP | 559785 | 9/1993 | EP | 673383 | 5/2000 |
| EP | 567541 | 11/1993 | EP | 996424 | 5/2000 |
| EP | 574185 | 12/1993 | EP | 1004572 | 5/2000 |
| EP | 577243 | 1/1994 | EP | 1004578 | 5/2000 |
| EP | 601486 | 6/1994 | EP | 1004580 | 5/2000 |
| EP | 604983 | 7/1994 | EP | 1004581 | 5/2000 |
| EP | 605729 | 7/1994 | EP | 1006187 | 6/2000 |
| EP | 301064 | 8/1994 | EP | 1022286 | 7/2000 |
| EP | 619371 | 10/1994 | EP | 1022336 | 7/2000 |
| EP | 620278 | 10/1994 | EP | 759937 | 8/2000 |
| EP | 623343 | 11/1994 | EP | 1029897 | 8/2000 |
| EP | 624646 | 11/1994 | EP | 938557 | 9/2000 |
| EP | 624647 | 11/1994 | EP | 1033364 | 9/2000 |
| EP | 624648 | 11/1994 | EP | 1041072 | 10/2000 |
| EP | 624649 | 11/1994 | EP | 1043333 | 10/2000 |
| EP | 628631 | 12/1994 | EP | 1046396 | 10/2000 |
| EP | 653935 | 5/1995 | EP | 1051082 | 11/2000 |
| EP | 510091 | 6/1995 | EP | 1074622 | 2/2001 |
| EP | 659883 | 6/1995 | EP | 1077259 | 2/2001 |
| EP | 210581 | 7/1995 | EP | 1077681 | 2/2001 |
| EP | 669831 | 9/1995 | EP | 1086947 | 3/2001 |
| EP | 682113 | 11/1995 | EP | 797437 | 4/2001 |
| EP | 687675 | 12/1995 | EP | 1088550 | 4/2001 |
| EP | 610334 | 1/1996 | EP | 1088819 | 4/2001 |
| EP | 694511 | 1/1996 | EP | 1090992 | 4/2001 |
| EP | 697819 | 2/1996 | EP | 1097928 | 5/2001 |

| | | |
|---|---|---|
| EP | 1104758 | 6/2001 |
| EP | 1104759 | 6/2001 |
| EP | 1104760 | 6/2001 |
| EP | 1104771 | 6/2001 |
| EP | 1106612 | 6/2001 |
| EP | 731808 | 7/2001 |
| EP | 862562 | 7/2001 |
| EP | 1113008 | 7/2001 |
| EP | 1113020 | 7/2001 |
| EP | 1114826 | 7/2001 |
| EP | 1118858 | 7/2001 |
| EP | 1127882 | 8/2001 |
| EP | 538297 | 9/2001 |
| EP | 800505 | 9/2001 |
| EP | 1132392 | 9/2001 |
| EP | 1134215 | 9/2001 |
| EP | 1138680 | 10/2001 |
| EP | 1142889 | 10/2001 |
| EP | 1145711 | 10/2001 |
| EP | 1146051 | 10/2001 |
| EP | 1148054 | 10/2001 |
| EP | 1149842 | 10/2001 |
| EP | 715653 | 11/2001 |
| EP | 836475 | 11/2001 |
| EP | 1153940 | 11/2001 |
| EP | 1161941 | 12/2001 |
| EP | 1167376 | 1/2002 |
| EP | 1167386 | 1/2002 |
| EP | 1178115 | 2/2002 |
| EP | 1188769 | 3/2002 |
| EP | 1191025 | 3/2002 |
| EP | 653935 | 5/2002 |
| EP | 1203580 | 5/2002 |
| EP | 814831 | 6/2002 |
| EP | 1032571 | 6/2002 |
| EP | 1225182 | 7/2002 |
| EP | 1227103 | 7/2002 |
| EP | 806964 | 8/2002 |
| EP | 1012151 | 8/2002 |
| EP | 724587 | 9/2002 |
| EP | 972020 | 9/2002 |
| EP | 1041972 | 9/2002 |
| EP | 1236739 | 9/2002 |
| EP | 1236797 | 9/2002 |
| EP | 1238984 | 9/2002 |
| EP | 1241261 | 9/2002 |
| EP | 706521 | 10/2002 |
| EP | 1077681 | 10/2002 |
| EP | 1245567 | 10/2002 |
| EP | 1247456 | 10/2002 |
| EP | 1247810 | 10/2002 |
| EP | 1251137 | 10/2002 |
| EP | 1258495 | 11/2002 |
| EP | 1258496 | 11/2002 |
| EP | 917534 | 12/2002 |
| EP | 1161940 | 12/2002 |
| EP | 1262177 | 12/2002 |
| EP | 1262180 | 12/2002 |
| EP | 1264843 | 12/2002 |
| GB | 180574 | 6/1921 |
| WO | WO 94/03160 | 2/1994 |
| WO | WO 95/12604 | 5/1995 |
| WO | WO 95/12605 | 5/1995 |
| WO | WO 95/14033 | 5/1995 |
| WO | WO 95/20953 | 8/1995 |
| WO | WO 95/20954 | 8/1995 |
| WO | WO 97/10224 | 3/1997 |
| WO | WO 97/17951 | 5/1997 |
| WO | WO 00/06126 | 7/1998 |
| WO | WO 98/46270 | 10/1998 |
| WO | WO 98/46588 | 10/1998 |
| WO | WO 98/47002 | 10/1998 |
| WO | WO 98/53798 | 12/1998 |
| WO | WO 99/04813 | 2/1999 |
| WO | WO 99/59551 | 5/1999 |
| WO | WO 99/29327 | 6/1999 |
| WO | WO 99/30690 | 6/1999 |
| WO | WO 99/33448 | 7/1999 |
| WO | WO 99/59544 | 11/1999 |
| WO | WO9959551 | 11/1999 |
| WO | WO 99/62499 | 12/1999 |
| WO | WO 99/62969 | 12/1999 |
| WO | WO 99/63969 | 12/1999 |
| WO | WO 00/02586 | 1/2000 |
| WO | WO 02/096401 A1 | 2/2000 |
| WO | WO 00/50020 | 8/2000 |
| WO | WO 01/49272 A2 | 7/2001 |
| WO | WO 01/74448 A1 | 10/2001 |
| WO | 1147879 | 10/2001 |
| WO | WO2001074448 | 10/2001 |
| WO | WO 01/80822 A2 | 11/2001 |
| WO | WO 01/83093 A1 | 11/2001 |
| WO | WO 01/89679 A2 | 11/2001 |
| WO | WO 01/98282 A1 | 12/2001 |
| WO | WO 02/03914 A2 | 1/2002 |
| WO | WO 02/09671 A2 | 2/2002 |
| WO | WO 02/26262 A2 | 4/2002 |
| WO | WO 02/28364 A2 | 4/2002 |
| WO | WO 02/28365 A2 | 4/2002 |
| WO | WO2002028364 | 4/2002 |
| WO | WO2002028365 | 4/2002 |
| WO | WO 02/45693 A1 | 6/2002 |
| WO | WO 02/056861 A2 | 7/2002 |
| WO | WO2002056861 | 7/2002 |
| WO | WO 01/059106 A1 | 8/2002 |
| WO | WO 01/064093 A2 | 8/2002 |
| WO | WO 02/064093 A2 | 8/2002 |
| WO | WO 02/067854 A2 | 9/2002 |
| WO | WO 02/069977 A1 | 9/2002 |
| WO | WO 02/096401 A1 | 12/2002 |

OTHER PUBLICATIONS

Surface Profile Parameters, Surface Meterology Guide—Profile Parameters, pp. 1–12 (Jan. 30, 2001).

Electropolishing, pp. 1–3 (Jan. 30, 2001).

A. Faure et al., *J. Pharm. Pharmacol.*, 50: (12) 1431–1432 (1998).

K. P. R. Chowdary and T. Manjula, Effect of Selected Binders and Disintegrants on the dissolution Rate of Nimesulide from Tablets, Indian J. Pharm. Sci., 62: (3) 224–228 (2000).

A. K. Dwivedi et al., Development of Stable Formulation of Picroliv, a new Hepatoprotective Agent, Indian *Journal of Pharmaceutical Science.*, 57: (2) 88–90 (Mar.–Apr. 1995).

A. E. Beezer et al., Letter to the Editor, "Comments on Serger et al.'s (1998, 1999) calorimetric stability studies," *International Journal of Pharmaceutics* 207/1–2: 117–118 (Oct 10, 2000).

G. Bardini et al., Letters, Effect of different Pharmacological formulations of Gliclazide on Postprandial Hyperglycaemia, *Diabetic Medicine* 15: (8) 706–708 (1998).

R. Ek et al., Letter to the Editor, Microcrystalline Cellulose as a Sponge as an Alternative Concept to the Crystallite–Gel Model for Extrusion and Spheronization, *Pharmaceutical Research*, 15: (4) 509–512 (1998).

R. S. Chapman and J. G. Ratcliffe, Brief technical note Covalent linkage of antisera to microparticulate cellulose using 1,1'-carbontyldimidazole: a rapid, practical method with potential use in solid–phase immunoassay, *Clinica Chimica Acta*, 118: (1) 129–134 (1982).

J. Seth et al., Simple Solid–Phase Radioimmunoassays for Total Tri–iodothyronine and Thyroxine in Serum, and their clinical evaluation, *Clinica Chimica Acta*, 68: (3) 291–301 (May 3, 1976).

M. Nakamura and Sachiya Ohtaki, Formation and Reduction of Ascorbate Radicals by Hog Thyuroid Microsomes, *Archives of Biochemistry and Biophysics*, 305: (1) 84–90, (Aug. 15, 1993).

R. S. Rapaka et al., Facile hydrolytic cleavage of N,O–di-heptafluorobutyryl derivatives of thyrodial amino acids, *Journal of Chromatography*, 236:496–498 (1982).

Thyroid Hormone, Synthetic Class 72120 Source: NDC Health's PhASt Combined Retail/Mail Order + Non–Retail for the years 2001 & 2002, pp. 1–6 (2002).

Obae, K. et al.: International Journal of Pharmaceutics, 182(199):155–164 (1999).

Ceolus, KG–801, Certificate of Analysis, Asahi Chemical Co., LTD, 1 page (Jan. 7, 1999), (Jun. 24, 2002).

Ceolus, KG–802, Certificate of Analysis, Asahi Kasei Corp., 1 page (Jun. 19, 2001), (Nov. 26, 2002).

Avicel, PH–101, Certificate of Analysis, FMC BioPolymer, 1 page (Aug. 21, 2001).

Avicel, PH–102, Certificate of Analysis, FMC BioPolymer, 1 page (Aug. 18, 2002).

Avicel, PH–301, Certificate of Analysis, FMC BioPolymer, 1 page (Date unavailable).

Ceolus™, Microcrystalline Cellulose, NF, Ph. Eur., JP, 6 pages (CEOL–Oct. 1997).

Introduction of Celous®, Microcrystalline Cellulose, NF/EP/JP, Asashi Chemical Industry Co., Ltd., 2 pages (Date unavailable).

New Microcrystalline Cellulose Products, Ceolus® KG, 15 pages (Date unavailable).

Asashi Chemical, Japan's leading supplier of pharmaceutical excipients, 10 pages (Nov. 2000).

Introduction of Celous® KG–802, Asashi Chemical, 4 pages (Date unavailable).

Introduction of Celphere®, Microcrystalline Cellulose, NF/EP, Microcrystalline Cellulose Spheres JPE, Asashi Chemical Industry Co., Ltd.,Asashi Chemical Industry Co., Ltd., 2 pages (Date unavailable).

Celphere®, Spherical Seed Core of MCC, Asahi Chemical, 15 pages (Date unavailable).

PCS®: Partly Pregelatinized Starch (JPE) Pregelelatinized Starch (NF,EP), 6 pages (Date unavailable).

Letter to Food and Drug Administration from Asahi Chemical Industry Co., LTD, Drug Master File 13834 for Ceolus KG™, 1 page (Feb. 19, 2000).

Stofer, Sheldon, S. and Szpunar, Walter E.: JAMA, 251(5):635–636 (1984).

Chong, Min Won: Pharmaceutical Research, 9(1):131–137(1992).

Brower, James F. et al.: J. Pharmaceutical Sciences, 73(9):1315–1317 (1984).

Richheimer, Steven L. and Amer, Tahani M.: J. Pharmaceutical Sciences, 72(11):1351–1353 (1983).

De Meijer, P.J.J.: Pharmaceutisch Weekbland, 116:1085–1089 (1981).

Das Gupta, V. et al.: J. Clinical Pharmacy and Therapeutics, 15:331–336 (1990).

Andre, M. et al.: J. Chromatography A, 725:287–294 (1996).

Federal Register, 65(157):43535–43538 (Aug. 14, 1997).

In the Matter of Asahi Chemical Industry Co., Ltd., FTC Order, pp. 1–9 (Date unavailable).

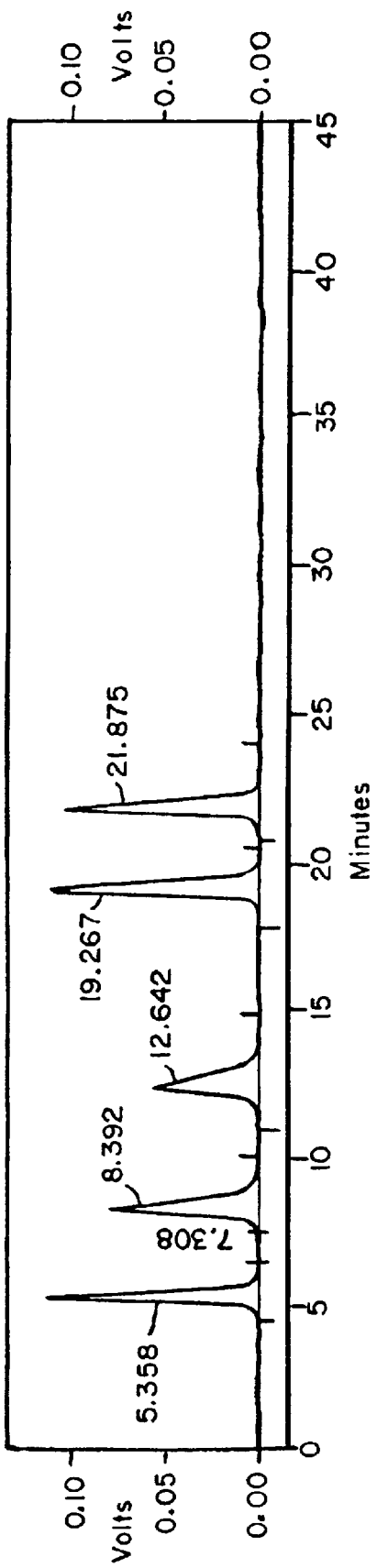
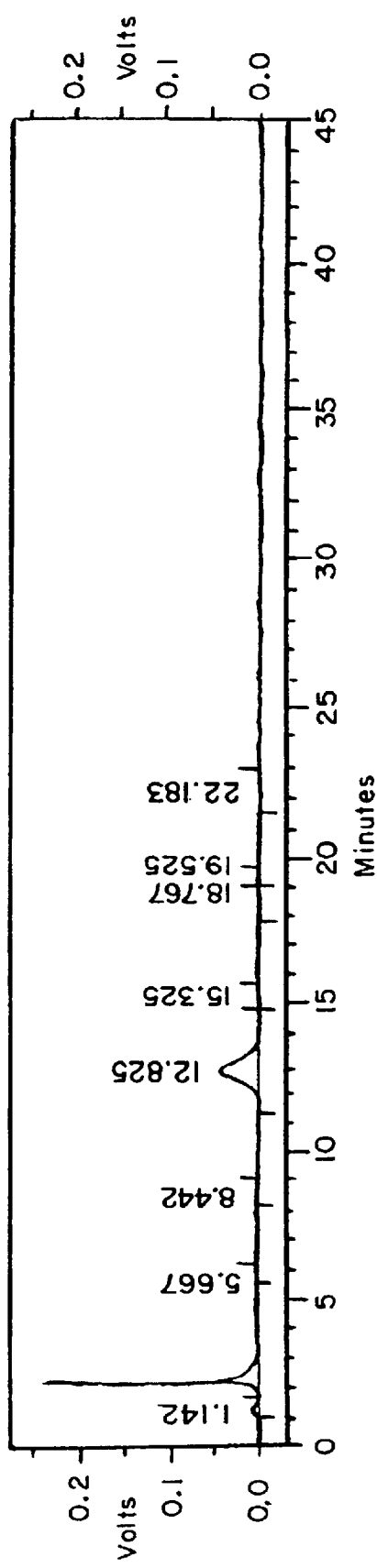
FIG. 5A
FIG. 5B

LEVOTHYROXINE COMPOSITIONS AND METHODS

RELATED U.S. PATENT APPLICATIONS

This application for U.S. patent relates to and claims benefit of U.S. Provisional application Nos. 60/269,009, filed on Feb. 15, 2001, No. 60/268,998, filed on Feb. 15, 2001, No. 60/311,523, filed on Aug. 10, 2001, No. 60/311,552, filed on Aug. 10, 2001, No. 60/311,549, filed on Aug. 10, 2001, No. 60/311,522, filed on Aug. 10, 2001, No. 60/311,524, filed on Aug. 10, 2001, No. 60/311,550, filed on Aug. 10, 2001, No. 60/311,525, filed on Aug. 10, 2001, No. 60/312,114, filed on Aug. 14, 2001, No. 60/312,113, filed on Aug. 14, 2001, No. 60/312,287, filed on Aug. 14, 2001, No. 60/312,184, filed on Aug. 14, 2001, No. 60/312,273, filed on Aug. 14, 2001, No. 60/312,206, filed on Aug. 14, 2001, No. 60/312,289, filed on Aug. 14, 2001, No. 60/312,483, filed on Aug. 15, 2001, No. 60/344,764, filed on Oct. 29, 2001, No. 60/344,763, filed on Oct. 29, 2001, No. 60/347,828, filed on Oct. 29, 2001, No. 60/345,344, filed on Oct. 29, 2001, No. 60/345,343, filed on Oct. 29, 2001, No. 60/344,762, filed on Oct. 29, 2001, No. 60/344,744, filed on Oct. 29, 2001, and No. 60/347,827, filed on Oct. 29, 2001.

FIELD OF THE INVENTION

The invention generally relates to stable pharmaceutical compositions, and methods of making and administering such compositions. In one aspect, the invention features stabilized pharmaceutical compositions that include pharmaceutically active ingredients, such as levothyroxine (T4) sodium and liothyronine (T3) sodium (thyroid hormone drugs), preferably in an immediate release solid dosage form. Also provided are methods for making and using such immediate release and stabilized compositions.

BACKGROUND

Thyroid hormone preparations of levothyroxine sodium and liothyronine sodium are pharmaceutical preparations useful to the treatment of hypothyroidism and thyroid hormone replacement therapy in mammals, for example, humans and dogs.

Thyroid hormone preparations are used to treat reduced or absent thyroid function of any etiology, including human or animal ailments such as myxedema, cretinism and obesity.

Hypothyroidism is a common condition. It has been reported in the United States Federal Register that hypothyroidism has a prevalence of 0.5 percent to 1.3 percent in adults. In people over 60, the prevalence of primary hypothyroidism increases to 2.7 percent in men and 7.1 percent in women. Because congenital hypothyroidism may result in irreversible mental retardation, which can be avoided with early diagnosis and treatment, newborn screening for this disorder is mandatory in North America. Europe, and Japan.

Thyroid hormone replacement therapy can be a chronic, lifetime endeavor. The dosage is established for each patient individually. Generally, the initial dose is small. The amount is increased gradually until clinical evaluation and laboratory tests indicate that an optimal response has been achieved. The dose required to maintain this response is then continued. The age and general physical condition of the patient and the severity and duration of hypothyroid symptoms determine the initial dosage and the rate at which the dosage may be increased to the eventual maintenance level. It has been reported that the dosage increase should be very gradual in patients with myxedema or cardiovascular disease to prevent precipitation of angina, myocardial infarction, or stroke.

It is important that thyroid hormone treatment have the correct dosage. Both under-treatment and over-treatment can have deleterious health impacts. In the case of under-treatment, a sub-optimal response and hypothyroidism could result. Under-treatment has also been reported to be a potential factor in decreased cardiac contractility and increased risk of coronary artery disease. Conversely, over-treatment may result in toxic manifestations of hyperthyroidism such as cardiac pain, palpitations, or cardiac arrhythmia's. In patients with coronary heart disease, even a small increase in the dose of levothyroxine sodium may be hazardous in a particular patient.

Hyperthyroidism is a known risk factor for osteoporosis. Several studies suggest that sub clinical hyperthyroidism in premenopausal women receiving thyroid hormone drugs for replacement or suppressive therapy is associated with bone loss. To minimize the risk of osteoporosis, it is preferable that the dose be kept to the lowest effective dose.

Because of the risks associated with over-treatment or under-treatment with levothyroxine sodium, there is a need for thyroid hormone products that are consistent in potency and bioavailability. Such consistency is best accomplished by manufacturing techniques that maintain consistent amounts of the active moiety during tablet manufacture.

Thyroid hormone drugs are natural or synthetic preparations containing tetraiodothyronine ($T_4$, levothyroxine) or triiodothyronine ($T_3$, liothyronine) or both, usually as their pharmaceutically acceptable (e.g., sodium) salts. $T_4$ and $T_3$ are produced in the human thyroid gland by the iodination and coupling of the amino acid tyrosine. $T_4$ contains four iodine atoms and is formed by the coupling of two molecules of diiodotyrosine (DIT). $T_3$ contains three atoms of iodine and is formed by the coupling of one molecule of DIT with one molecule of monoiodotyrosine (MIT). Both hormones are stored in the thyroid colloid as thyroglobulin. Thyroid hormone preparations belong to two categories: (1) natural hormonal preparations derived from animal thyroid, and (2) synthetic preparations. Natural preparations include desiccated thyroid and thyroglobulin.

Desiccated thyroid is derived from domesticated animals that are used for food by man (either beef or hog thyroid), and thyroglobulin is derived from thyroid glands of the hog. The United States Pharmacopoeia (USP) has standardized the total iodine content of natural preparations. Thyroid USP contains not less than (NLT) 0.17 percent and not more than (NMT) 0.23 percent iodine, and thyroglobulin contains not less than (NLT) 0.7 percent of organically bound iodine. Iodine content is only an indirect indicator of true hormonal biologic activity.

Synthetic forms for both $T_4$ and $T_3$ thyroid hormone are available from a number of producers. For example, liothyronine sodium ($T_3$) tablets are available under the trademark Cytomels from King Pharmaceuticals, Inc., St. Louis, Mo. Levothyroxine sodium ($T_4$) is available under the tradename Levoxyl® from King Pharmaceuticals, Inc., under the tradename Synthroid® from Knoll Pharmaceutical, Mt. Olive, N.J., and under the tradename Unithroid® from Jerome Stevens Pharmaceuticals, Bohemia, N.Y. In addition a veterinarian preparation of levothyroxine sodium is available under the tradename Soloxine® from King Pharmaceuticals, Inc.

Levoxyl® (levothyroxine sodium tablets,USP) contain synthetic crystalline L-3,3',5,5'-tetraiodothyronine sodium salt [levothyroxine ($T_4$) sodium]. As indicated above, the synthetic $T_4$ in Levoxyl® is identical to that produced in the human thyroid gland. The levothyroxine ($T_4$) sodium in Levoxyl® has an empirical formula of $C_{15}H_{10}I_4N NaO_4 \cdot H_2O$, a molecular weight of 798.86 g/mol (anhydrous), and a structural formula as shown:

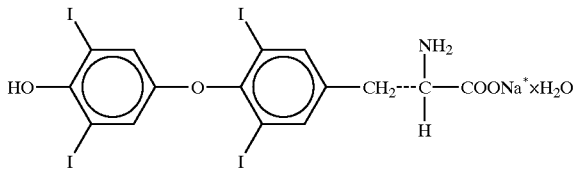

It is well known that the stability of thyroid hormone drugs is quite poor. They are hygroscopic and degrade in the presence of moisture or light, and under conditions of high temperature. The instability is especially notable in the presence of pharmaceutical excipients, such as carbohydrates, including lactose, sucrose, dextrose and starch, as well as certain dyes. The critical nature of the dosage requirements, and the lack of stability of the active ingredients in the popular pharmaceutical formulations, have led to a crisis which has adversely effected the most prescribed thyroid drug products. See, e.g., 62 Fed. Reg. 43535 (Aug. 14, 1997).

It is desirable, therefore, to prepare a stabilized dosage of levothyroxine and liothyronine, which will have a longer shelf life that can be used in the treatment of human or animal thyroid hormone deficiency. U.S. Pat. No. 5,225,204 (the '204 patent) is directed to improving the stability of levothyroxine sodium. In one embodiment disclosed by the '204 patent, stabilized levothyroxine sodium was prepared in a dry state by mixing levothyroxine sodium with a cellulose tableting agent using geometric dilution and subsequently combining this mixture with the same or a second cellulose tableting agent, such as microcrystalline cellulose. Other tableting aids or excipients can be used in this formulation. The '204 patent is incorporated by reference herein, in its entirety.

The microcrystalline cellulose disclosed in the '204 patent is AVICEL 101®, AVICEL 102®, AVICEL 103®, AVICEL 105®, trademarks of FMC Company of Newark, Del., and Microcrystalline Cellulose NF, or EMCOCEL®, a trademark owned by Penwest Pharmaceuticals of Patterson, N.Y. These microcrystalline cellulose products are prepared by re-slurrying the cellulose and spray drying the product. This produces an α-helix spherical microcrystalline cellulose product.

U.S. Pat. Nos. 5,955,105 and 6,056,975 (the continuation of '105) disclose pharmaceutical preparations of levothyroxine and microcrystalline cellulose, along with other excipients. The microcrystalline cellulose products used in the '105 and '975 patents were also the α-form Avicel microcrystalline cellulose products. U.S. Pat. Nos. 5,955, 105 and 6,056,975 are incorporated by reference herein, in their entirety.

Another microcrystalline cellulose product is a β-sheet form microcrystalline cellulose having a flat needle shape, marketed under the trademark CEOLUS KG801® by FMC Company of Newark, Del. The Ceolus® product has different morphology, and different performance characteristics, than those of the Avicel product. The β-sheet microcrystalline cellulose of the present invention is disclosed in U.S. Pat. No. 5,574,150, which is hereby incorporated by reference. Further disclosure relating to β-sheet microcrystalline cellulose is found in *International Journal of Pharmaceutics*, 182:155–164 (1999), which is hereby incorporated by reference.

The Ceolus® product (β-sheet microcrystalline cellulose) is disclosed by FMC, in its product bulletin dated October 1997, as being suitable for "smaller size tablets" and "exceptional drug carrying capacity." The Ceolus® product was said to provide superior compressibility and drug loading capacity, that still exhibited effective flowability. The examples given in the Ceolus® bulletin were of vitamin C combined with Ceolus® microcrystalline cellulose at levels of from 30 to 45 weight % Ceolus® product in the form of a tablet.

However, there have been problems using the Ceolus® product. For example, at higher levels of Ceolus® product concentration, flow problems were encountered in the process of compressing tablets, and the Ceolu® product was considered unsuitable for compression at higher concentrations than about 45 weight %.

There is a definite need for solid levothyroxine (T4) and/or liothyronine (T3) (thyroid hormone drugs) pharmaceutical compositions, preferably in an immediate release solid dosage form, with the T4 and T3 in the form of their sodium salts that are relatively stable. There is also a need for methods for making such immediate release and stabilized solid levothyroxine (T4) and/or liothyronine (T3) (thyroid hormone drugs) pharmaceutical compositions.

SUMMARY OF THE INVENTION

The present invention overcomes and alleviates the above-mentioned drawbacks and disadvantages in the thyroid drug art through the discovery of novel oral levothyroxine (T4) and/or liothyronine (T3) (thyroid hormone drugs) pharmaceutical compositions and methods.

Generally speaking, the present invention relates to stabilized solid levothyroxine (T4) sodium and/or liothyronine (T3) sodium (thyroid hormone drugs) pharmaceutical compositions and in particular, immediate release, stabilized pharmaceutical compositions that include pharmaceutically active ingredients, such as levothyroxine (T4) sodium and/or liothyronine (T3) sodium (thyroid hormone drugs). Preferably, but not necessarily, the novel pharmaceutical compositions are provided in a solid dosage form, such as a tablet.

The pharmaceutical compositions of the present invention are useful for, among other things, replacement or supplemental therapy in hypothyroidism of any etiology, except transient hypothyroidism during the recovery phase of subacute thyroiditis, suppression of pituitary TSH secretion in the treatment or prevention of various types of euthyroid goiters, including thyroid nodules, Hashimoto's thyroiditis, multinodular goiter and adjunctive therapy in the management of thyrotropin-dependent well-differentiated thyroid cancer in warm-blooded animals, especially humans including pediatrics.

The present invention also provides methods for making such immediate release and stabilized levothyroxine (T4) sodium and/or liothyronine (T3) sodium (thyroid hormone drugs) pharmaceutical compositions.

Also in accordance with the present invention, because of the extraordinary release characteristics of the preferred compositions, a method of administration to children and patients who have difficulty taking pills, wherein the solid composition having the appropriate dosage in accordance with the present invention is simply put in an aqueous fluid, e.g., juice, where it dissolves in a matter of 1–3 minutes, so that the patient can then ingest the fluid, and receive the appropriate dosage, is now made practical.

The present invention has a wide range of important uses including providing pharmaceutically active levothyroxine compositions with enhanced bioavailability, improved shelf life, and more reliable potency.

We have discovered immediate release pharmaceutical compositions that include as pharmaceutically active ingredients at least one of levothyroxine and liothyronine, preferably at least one levothyroxine salt, as the major active ingredient. Such preferred immediate release compositions desirably provide at least about 85% (w/v) dissolution of the levothyroxine salt in less than about 20 minutes as determined by standard assays disclosed herein. Surprisingly, it has been found that by combining the pharmaceutically active ingredients with specific additives in accordance with the invention, it is possible to formulate the compositions so that the ingredients are released almost immediately after ingestion or contact with an aqueous solution, e.g., in a matter of minutes. Preferred invention compositions are stable and provide better shelf life and potency characteristics than prior pharmaceutical compositions.

The immediate release pharmaceutical compositions of the invention provide important uses and advantages. A major advantage is the stability of the active ingredients in the composition. For example, while, as indicated above, prior formulations with sugars, starches, and various types of celluloses, including micro-cellular celluloses, such as the Avicel products, have experienced substantial degradation of the active ingredients, e.g. T4 sodium. To deal with this problem, pharmaceutical manufacturers have overformulated the T4-containing pharmaceutical compositions containing such active ingredients, so that the patient can obtain at least the prescribed dosage despite the carbohydrate-induced instability of the active ingredient. However, the patient who obtains the pharmaceutical immediately after it is made, receives an over-dosage of the active compound; whereas, the patient who has received the pharmaceutical after it has sat on the pharmacy shelf for an extended period, will receive an under-dosage of the active ingredient. In either case, the patient receives the wrong dosage, with possible serious consequences.

In sharp contrast, it has been surprisingly found that the use of the β-sheet microcrystalline cellulose in the compositions of the present invention substantially increases the stability of the thyroid hormone drugs, so that the patient obtains consistent potency over an extended shelf life, compared to prior thyroid hormone drug products. In this application, the term "stabilized", as applied to levothyroxine and/or liothyronine, means that the loss of potency over the shelf life of the product is less than about 0.7% potency per month, for at least about 18 months. Preferred compositions have a loss of potency of less than about 0.5% per month for such a period, and more preferred compositions have a loss of potency of less than about 0.3% per month for such a period.

Further, the compositions of the invention provide favorable pharmacokinetic characteristics when compared to prior formulations. In particular, the immediate release pharmaceutical compositions that include levothyroxine salt are more quickly available for absorption by the gastrointestinal (GI) tract and are absorbed more completely than has heretofore been possible. This invention feature substantially enhances levothyroxine bioavailability, thereby improving efficacy and reliability of many standard thyroid hormone replacement strategies.

Additionally, the desirable immediate release characteristics of the present invention facilitate dosing of patients who may be generally adverse to thyroid hormone replacement strategies involving solid dosing. More specifically, immediate release pharmaceutical compositions disclosed herein can be rapidly dissolved in an appropriate aqueous solution (e.g., water, saline, juice) or colloidal suspension (e.g., baby formula or milk) for convenient administration to such patients. Illustrative of such patients include infants, children, and adults who may experience swallowing difficulties. The invention thus makes standard thyroid hormone replacement strategies more flexible and reliable for such patients.

Accordingly, and in one embodiment, the invention features an immediate release pharmaceutical composition comprising at least one levothyroxine, preferably one of such a salt. At least about 80% of the levothyroxine dissolves in aqueous solution in less than about 20 minutes as determined by a standard assay, disclosed herein. Preferably, at least about 80% of the levothyroxine is dissolved in the aqueous solution by about 15 minutes from the time that the composition, in pill form, is placed in the aqueous solution. More preferably, at least about 85% of the levothyroxine is released to the aqueous solution by about 10 minutes, most preferably by about 5 minutes after exposure of the composition to the aqueous solution. As shown below, compositions in accordance with the present invention can be formulated to release 85% of the levothyroxine within 2–3 minutes after exposure to the aqueous solution.

It has been found that by combining one or more of the pharmaceutically active agents with β-form microcrystalline cellulose, it is possible to produce compositions with favorable immediate release characteristics. Without wishing to be bound to theory, it is believed that the agents do not bind well to certain grades of the β-sheet form microcrystalline cellulose. More of the agent is thus available for immediate release. In contrast, it is believed that many prior formulations have active agents that bind cellulose additives, making less available. The release characteristics of the compositions of the invention are also improved by the use of other agents, as discussed further below.

Thus, in one embodiment, the present invention relates to a stabilized pharmaceutical composition comprising a pharmaceutically active ingredient, such as levothyroxine, and the β-sheet form of microcrystalline cellulose, in the form of a solid dosage. More specifically, the present invention relates to a stabilized pharmaceutical composition comprising a pharmaceutically active ingredient, such as levothyroxine sodium and/or liothyronine sodium, at least about 50 weight % of the dosage weight composed of the β-sheet form of microcrystalline cellulose, and, optionally, additional excipients, in a solid dosage form.

In another aspect, the invention provides an aqueous solution or colloidal suspension that includes at least one of the compositions of this invention, preferably between from about one to about five of same, more preferably about one of such compositions.

It has also been found that β-sheet microcrystalline cellulose grades having preferred bulk densities provide for more compact processing than use of other celluloses. That is, use of the β-sheet microcrystalline cellulose having bulk densities in accord with this invention helps to provide for higher compression ratios (initial volume/final volume). As discussed below, other invention aspects help reduce or avoid production of damaging compression heat that has damaged prior formulations made from high compression ratios. The compositions of the present invention generally also require less compressional force to form the tablets.

Accordingly, the invention also provides methods for making an immediate release pharmaceutical composition comprising at least one levothyroxine, preferably one of such a salt. In one embodiment, the method includes at least one and preferably all of the following steps:

a) mixing a levothyroxine salt with microcrystalline β-cellulose and preferably a croscarmellose salt to make a blend; and b) compressing the blend in a ratio of initial volume to final volume of between from about 2:1 to about 5:1 to make the composition, preferably about 4:1.

In one embodiment, the method involves preparing an oral dosage form of a pharmaceutically active ingredient comprising dry blending the pharmaceutically active ingredient and at least about 50 weight % of the β-sheet form of microcrystalline cellulose, and compressing the blend to form a solid dosage.

These and other objects, features, and advantages of the present invention may be better understood and appreciated from the following detailed description of the embodiments thereof, selected for purposes of illustration and shown in the accompanying figures and examples. It should therefore be understood that the particular embodiments illustrating the present invention are exemplary only and not to be regarded as limitations of the present invention.

BRIEF DESCRIPTION OF THE DRAWINGS

The foregoing and other objects, advantages and features of the invention, and the manner in which the same are accomplished, will become more readily apparent upon consideration of the following detailed description of the invention taken in conjunction with the accompanying Figs., which illustrate a preferred and exemplary embodiment, wherein:

FIG. 5A is a chromatogram showing various levothryoxine impurity standards; and

FIG. 5B is a chromatograph showing results of a levothyroxine sodium sample made in accordance with the present invention.

DETAILED DESCRIPTION

Figure 1A:
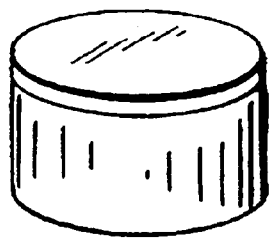
FIGS. 1A–1C illustrate various solid dosage forms such as cylindrical tablets and raised violin shaped tablets.
Figure 1B:
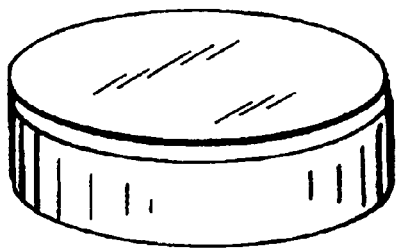

By way of illustrating and providing a more complete appreciation of the present invention and many of the attendant advantages thereof, the following detailed description is given concerning the novel oral levothyroxine (T4) and/or liothyronine (T3) (thyroid hormone drugs) pharmaceutical compositions and methods for use in warm-blooded animals, especially humans and children.

As discussed, the invention relates to immediate release solid pharmaceutical compositions, such as stabilized pharmaceutical compositions, that include pharmaceutically active ingredients, such as levothyroxine (T4) sodium and liothyronine (T3) sodium (thyroid hormone drugs), preferably in a solid dosage form. Also provided are methods for making such immediate release and stabilized compositions.

Aspects of the present invention have been disclosed in U.S. Provisional Application No. 60/269,089, entitled Stabilized Pharmaceutical and Thyroid Hormone Compositions and Method of Preparation and filed on Feb. 15, 2001 by Franz, G. A. et al. The disclosure of said provisional application is incorporated herein by reference.

By the phrase "immediate release" is meant a pharmaceutical composition in which one or more active agents therein demonstrates at least about 80% (w/v) dissolution, preferably between from about 90% (w/v) to about 95% (w/v), more preferably about 95% (w/v) to about 99% (w/v) or more within 15 to 20 minutes as determined by a standard dissolution test. Suitable standard dissolution tests are known in the field. See FDA, Center for Drug Research, Guidance for Industry, *In Vivo Pharmacokinetics and Bioavailability Studies and In Vitro Dissolution Testing for Levothyroxine Sodium Tablets*, available at www.fda.gov/cder/guidance/index.htm. A specifically preferred dissolution test is provided in Example 2, below.

A pharmaceutical composition of the invention is "stable" or "stabilized" if one or more of the active agents therein exhibit good stability as determined by a standard potency test. More specifically, such compositions exhibit a potency loss of less than about 15%, preferably less than about 10%, more preferably less than about 1% to about 5% as determined by the test. Potency can be evaluated by one or a combination of strategies known in the field. See the USP. A preferred potency test compares loss or conversion of the active agent in the presence (experimental) or absence (control) of a carrier or excipient. A specifically preferred potency test is provided in Examples 1 and 3, below.

In preferred embodiments, the pharmaceutical compositions of the invention include, as an active agent, levothyroxine (T4), preferably a salt thereof such as levothyroxine sodium USP. Such compositions typically exhibit a levothyroxine (T4) plasma Cmax of between from about 12 μg/dl to about 16 μg/dl, preferably as determined. by the standard Cmax test. Preferably, the ln(Cmax) of the levothyroxine (T4) plasma level is between from about 1 to about 3.

The standard Cmax test can be performed by one or a combination of strategies known in the field. See e.g., the USP. A preferred Cmax test is disclosed below in Examples 8 and 9.

Additionally preferred compositions in accord with the invention provide a triiodothyronine (T3) plasma Cmax of between from about 0.1 ng/ml to about 10 ng/ml, preferably 0.5 ng/ml to about 2 ng/ml, as determined by the standard Cmax test. Typically, the ln(Cmax) is between from about 0.01 to about 5. See Examples 8 and 9 for more information.

Further preferred compositions exhibit a levothyroxine (T4) plasma Tmax of between from about 0.5 hours to about 5 hours, preferably as determined by a standard Tmax test. The standard Tmax test can be performed by procedures generally known in the field. See e.g., the USP. A preferred Tmax test is disclosed below in Examples 8 and 9.

Still further preferred compositions of the invention exhibit a triiodothyronine (T3) plasma Tmax of between from about 10 hours to about 20 hours, preferably of between from about 12 to about 16 hours as determined by the standard Tmax test.

Additionally, preferred invention compositions feature a levothyroxine (T4) plasma AUC (0-t) of between from about 450 μg-hour/dl to about 600 μg-hour/dl, preferably of between from 500 μg-hour/dl to about 550 μg-hour/dl, as determined by a standard AUC (0-t) test. Preferably, the ln[AUC(0-t)] is between from about 1 to about 10.

Standard methods for performing AUC (0-t) test determinations are generally known in the field. See e.g., the USP. Examples 8 and 9 below provide a specifically preferred method of determining the AUC (0-t).

Further, preferred invention compositions feature a triiodothyronine (T3) AUC (0-t) of between from about 10 ng-hour/ml to about 100 ng-hour/ml, preferably between from 20 ng-hour/ml to about 60 ng-hour/ml, as determined by the standard AUC (0-t) test. Preferably, the ln[AUC(0-t)] is between from about 1 to about 5.

As will be appreciated, many prior pharmaceutical formulations include lactose or other sugars as a pharmaceutically acceptable carrier. It has been found, however, that sugars such as lactose can react with active agents including the levothyroxine (T4) compositions of the present invention. For example, and without wishing to be bound to theory, it is believed that lactose is particularly damaging to T4 and T3 molecules via Schiff reactions. The invention addresses this problem by providing compositions that are essentially sugar-free. Particular invention compositions are essentially free of lactose.

Additionally, preferred pharmaceutical compositions of the invention are provided in which the active material is a non-granulated material. Prior levothyroxine compositions have been granulated in various size reduction machines to grains of less than, e.g., 5–20 microns average particle size in order to be effectively incorporated into the administrable pharmaceutical composition. The granulation process subjects the active material to degrading heat, which can have adverse effects on the active material, as well as reducing the activity level. Prior manufacturers purchase micronized levothyroxine manufactured under DMF No. 4789, and then granulate it before incorporating it into the levothyroxine pharmaceutical product.

In the preferred method of the present invention, the raw material is not granulated before incorporation into the pharmaceutical composition. Rather, the ingredients of the preferred pharmaceutical are mixed and the mixture is subjected to direct compression to form the pharmaceutical tablets of appropriate dosage. As a result, the activity of the active ingredient is not degraded prior to the direct compression step. Bulk levothyroxine is obtained in a fine powdered form, preferably from Biochemie GmbH, A-6250 Kundi, Austria. More importantly, the use of the preferred process results in a product which is immediately dispersible in aqueous solution, to make the active ingredient available for absorption in the body. As used in this application, "non-granulated" means that the bulk USP compound is used without subjecting it to granulators or similar high-energy size reduction equipment before being mixed with the other pharmaceutical components and formed into the appropriate pill. Preferably, the bulk active ingredient is mixed with the appropriate amounts of other ingredients and directly compressed into pill form. Since it is not necessary to granulate the material, it is not necessary to subject it to degrading temperatures in the process of forming the pharmaceutical compositions containing the active materials. In the present process, we start with micronized active material, which merely needs to be blended with the β-microcrystalline cellulose particles and other materials and then compressed. Others have to be granulated, and then dried, which steps interfere with the dissolution of the active material. The drying temperatures employed in manufacturing other active ingredients can cause degradation of the levothyroxine, as experienced in other available thyroxine compositions. It has been found that providing the invention compositions in a non-granulated format helps to reduce or eliminate active agent degradation, presumably by facilitating a reduction in friction, and thus degrading heat, during compression of the compositions into pills.

Practice of the invention is compatible with several β-form microcrystalline cellulose grades. Preferably, the β-form microcrystalline cellulose has a bulk density of between from about 0.10 g/cm$^3$ to about 0.35 g/cm$^3$, more preferably between from about 0.15 g/cm$^3$ to about 0.25 g/cm$^3$, still more preferably between from about 0.17 g/cm$^3$ to about 0.23 g/cm$^3$, most preferably between from about 0.19 g/cm$^3$ to about 0.21 g/cm$^3$.

Further preferred grades of the β-form microcrystalline cellulose are substantially non-conductive. Preferably, the β-form microcrystalline cellulose has a conductivity of less than about 200 μS/cm, more preferably, less than about 75 μS/cm, still more preferably between from about 0.5 μS/cm to 50 μS/cm, most preferably between from about 15 μS/cm to 30 μS/cm.

A specifically preferred β-form microcrystalline cellulose is sold by Asahi Chemical Industry Co., Ltd (Tokyo, Japan) as Ceolus® (Type KG-801 and/or KG-802).

Additionally, preferred compositions of the invention have a post-packaging potency of between from about 95% to about 120%, preferably 98% to about 110%, as determined by the standard potency test.

The present invention is a pharmaceutical product that is in the form of a solid dosage, such as a sublingual lozenge, a buccal tablet, an oral lozenge, a suppository or a compressed tablet. The pharmaceutically active ingredient is dry mixed with the β-form of the microcrystalline cellulose, optionally with additional excipients, and formed into a suitable solid dosage.

Preferred tablets according to the invention have a total hardness of between from about 1 to about 30 KP, preferably between from about 6 to about 14 KP as determined by a standard hardness test. Methods for determining tablet hardness are generally known in the field. See e.g., the USP. A preferred standard hardness test is disclosed below in Example 4.

Additionally, preferred pharmaceutical compositions including those in tablet format preferably include less than about 10% total impurities, more preferably less than about 5% of same, as determined by a standard impurity test.

Reference herein to the "standard impurity test" means a USP recognized assay for detecting and preferably quantitating active drug degradation products. In embodiments in which levothyroxine or liothyronine break-downs are to be monitored, such products include, but are not limited to, at least one of diiodothyronine (T2), triiodothyronine (T3), levothyroxine, triiodothyroacetic acid amide, triiodothyroethylamine, triiodothyroacetic acid, triiodothyroethyl alcohol, tetraiodothyroacetic acid amide, tetraiodothyroacetic acid, triiodothyroethane, and tetraiodothyroethane. Of particular interest are diiodothyronine (T2), triiodothyronine (T3), triiodothyroacetic acid, and tetraiodothyroacetic acid impurities.

A preferred impurity test for monitoring levothyroxine and liothyronine breakdown products involves liquid chromatography (LC) separation and detection, more preferably HPLC. Specifically preferred impurity tests are provided below in Examples 5 and 6.

Further preferred compositions in accord with the invention include one or more standard disintegrating agents, preferably croscarmellose, more preferably a salt of same. Still further preferred compositions include a pharmaceutically acceptable additive or excipient such as a magnesium salt.

The present invention can be prepared as a direct compression formula, dry granulation formnula, or as a wet granulation formula, with or without preblending of the drug, although preferably with preblending.

The pharmaceutically active ingredient can be any type of medication which acts locally in the mouth or systemically, which is the case of the latter, can be administered orally to transmit the active medicament into the gastrointestinal tract and into the blood, fluids and tissues of the body. Alternatively, the medicament can be of any type of medication which acts through the buccal tissues of the mouth to transmit the active ingredient directly into the blood stream thus avoiding first liver metabolism and by the gastric and intestinal fluids which often have an adverse inactivating or destructive action on many active ingredients unless they are specially protected against such fluids, as by means of an enteric coating or the like. The active ingredient can also be of a type of medication which can be transmitted into the blood circulation through the rectal tissues.

Representative active medicaments include antacids, antimicrobials, coronary dilators, peripheral vasodilators, antipsychotropics, antimanics, stimulants, antihistamines, laxatives, decongestants, vitamins, gastrosedatives, antidiarrheal preparations, vasodilators, antiarrythmics, vasoconstrictors and migraine treatments, anticoagulants and antithrombotic drugs, analgesics, antihypnotics, sedatives, anticonvulsants, neuromuscular drugs, hyper and hypoglycemic agents, thyroid and antithyroid preparations, diuretics, antispasmodics, uterine relaxants, mineral and nutritional additives, antiobesity drugs, anabolic drugs, erythropoietic drugs, antiasthematics, expectorants, cough suppressants, mucolytics, antiuricemic drugs, and drugs or substances acting locally in the mouth.

Typical active medicaments include gastrointestinal sedatives, such as metoclopramide and propantheline bromide, antacids, such as aluminum trisilicate, aluminum hydroxide and cimetidine, asprin-like drugs, such as phenylbutazone, indomethacin, and naproxen, ibuprofen, flurbiprofen, diclofenac, dexamethasone, prednisone and prednisolone, coronary vasodialator drugs, such as glyceryl trinitrate, isosorbide dinitrate and pentaerythritol tetrafitrate, peripheral and cerebral vasodilators, such as soloctidilum, vincamine, naftidroftiryl oxalate, comesylate, cyclandelate, papaverine and nicotinic acid, antimicrobials, such as erythromycin stearate, cephalexin, nalidixic acid, tetracycline hydrochloride, ampicillin, flucolaxacillin sodium, hexamine mandelate and hexamine hippurate, neuroleptic drugs, such as fluazepam, diazepam, temazepam, amitryptyline, doxepin, lithium carbonate, lithium sulfate, chlorpromazine, thioridazine, trifluperazine, fluphenazine, piperothiazine, haloperidol, maprotiline hydrochloride, imipramine and desmethylimipramine, central nervous stimulants, such as methylphenidate, ephedrine, epinephrine, isoproterenol, amphetamine sulfate and amphetamine hydrochloride, anitihistamine drugs, such as diphenylhydramine, diphenylpyramine, chlorpheniramine and brompheniramine, antidiarrheal drugs, such as bisacodyl and magnesium hydroxide, the laxative drug, dioctyl sodium sulfosuccinate, nutritional supplements, such as ascorbic acid, alpha tocopherol, thiamine and pyridoxine, antispasmotics, such as dicyclomine and diphenoxylate, drugs effecting the rhythm of the heart, such as verapamil, nifedepine. diltiazem, procainamide, disopyramide, bretylium tosylate, quinidine sulfate and quinidine gluconate, antihypertensive drugs, such as propranolol hydrochloride, guanethidine monosulphate, methyldopa, oxprenolol hydrochloride, captopril, Altace® and hydralazine, drugs used in the treatment of migraine, such as ergotamine, drugs effecting coagulability of blood, such as epsilon aminocaproic acid and protamine sulfate, analgesic drugs, such as acetylsalicyclic acid, acetaminophen, codeine phosphate, codeine sulfate, oxycodone, dihydrocodeine tartrate, oxydodeinone, morphine, heroin, nalbuphine, butorphanol tartrate, pentazocine hydrochloride, cyclazacine, pethidine, buprenorphine, scopolamine and mefenamic acid, antiepileptic or antiseizure drugs, such as phenytoin sodium and sodium valproate, neuromuscular drugs, such as dantrolene sodium, substances used in the treatment of diabetes, such as tolbutamide, diabenase glucagon and insulin, drugs used in the treatment of thyroid gland dysfunction, such as triiodothyronine, liothyronine sodium, levothyroxilne sodium and related compounds, and propylthiouracil, diuretic drugs, such as furosemide, chlorthalidone, hydrochlorthiazide, spironolactone and triampterene, the uterine relaxant drug ritadrine, appetite suppressants, such as fenfluramine hydrochloride, phentermine and diethylproprion hydrochloride, antiasthma drugs such as aminophylline, theophylline, salbutamol, orciprenaline sulphate and terbutaline sulphate, expectorant drugs, such as guaiphenesin, cough suppressants, such as dextromethorphan and mescaline, mucolytic drugs, such as carbocisteine, antiseptics, such as cetylpyridinium chloride, tyrothricin and chlorhexidine, decongestant drugs, such as phenylpropanolamine and pseudoephedrine, hypnotic drugs, such as dichloralphenazone and nitrazepam, antiemetic drugs, such as promethazine, haemopoetic drugs, such as ferrous sulphate, folic acid and calcium gluconate, uricosuric drugs, such as sulphinpyrazine, allopurinol and probenecid, and the like. It is understood that the invention is not restricted to the above medications.

The amount of pharmaceutically active ingredient in the present composition can vary widely, as desired. Preferably, the active ingredient is present in a composition of the present invention in an effective dosage amount. Exemplary of a range that the active ingredient may be present in a composition in accordance with the present invention is from about 0.000001 to about 10 weight %. More preferably, the amount of active ingredient is present in the range of about 0.001 to 5 weight %.

Of course, it should be understood that any suitable pharmaceutically acceptable form of the active ingredient can be employed in the compositions of the present invention, i.e., the free base or a pharmaceutically acceptable salt thereof, e.g., levothyroxine sodium salt, etc.

When the pharmaceutically active moiety is levothyroxine sodium, the preferred amount of the active moiety in the composition is present in the range of about 0.00005 to about 5 weight %. The more preferred range is from about 0.001 to about 1.0 weight %, and the most preferred range is from about 0.002 to about 0.6 weight % levothyroxine. The minimum amount of levothyroxine can vary, so long as an effective amount is utilized to cause the desired pharmacological effect. Typically, the dosage forms have a content of levothyroxine in the range of about 25 to 300 micrograms per 145 milligram pill for human applications, and about 100 to 800 micrograms per 145 mg pill for veterinary applications.

In accordance with the present invention, a goal of levothyroxine replacement therapy is to achieve and maintain a clinical and biochemical euthyroid state, whereas a goal of suppressive therapy is to inhibit growth and/or function of abnormal thyroid tissue. A dose of levothyroxine that is adequate to achieve these goals depends of course on a variety of factors including the patient's age, body weight, cardiovascular status, concomitant medical conditions, including pregnancy, concomitant medications, and the specific nature of the condition being treated. Hence, the following recommendations serve only as dosing guidelines. It should be understood by those versed in this art that dosing should be individualized and adjustments made based on periodic assessment of a patient's clinical response and laboratory parameters.

Preferably, but not necessarily, when using levothyroxine to treat, it should be taken in the morning on an empty stomach, at least one-half hour before any food is eaten. In addition, levothyroxine is preferably taken at least about 4 hours apart from drugs that are known to interfere with its absorption.

Due to the long half-life of levothyroxine, the peak therapeutic effect at a given dose of levothyroxine sodium may not be attained for about 4 to about 6 weeks.

In people older than 50 years, who have been recently treated for hyperthyroidism or who have been hypothyroid for only a short time (such as a few months), the average full replacement dose of levothyroxine sodium is approximately 1.7 mcg/kg/day (e.g., about 100 to about 125 mcg/day for a 70 kg adult). Older patients may require less than 1 mcg/kg/day. Levothyroxine sodium doses greater than about 200 mcg/day may or may not be required.

For most patients older than 50 years or for patients under 50 years of age with underlying cardiac disease, an initial starting dose of about 25 to about 50 mcg/day of levothyroxine sodium is recommended, with gradual increments in dose at about 6 to about 8 week intervals, as needed. The recommended starting dose of levothyroxine sodium in elderly patients with cardiac disease is about 12.5 to about 25 mcg/day, with gradual dose increments at about 4 to about 6 week intervals. The levothyroxine sodium dose is generally adjusted in about 12.5 to about 25 mcg increments until the patient with primary hypothyroidism is clinically euthyroid and the serum TSH has normalized.

In patients with severe hypothyroidism, the recommended initial levothyroxine sodium dose is about 12.5 to about 25 mcg/day with increases of about 25 mcg/day about every 2 to about 4 weeks, accompanied by clinical and laboratory assessment, until the TSH level is normalized.

In patients with secondary (pituitary) or tertiary (hypothalamic) hypothyroidism, the levothyroxine sodium dose should be titrated until the patient is clinically euthyroid and the serum free-$T_4$ level is restored to the upper half of the normal range.

In children, levothyroxine therapy may be instituted at full replacement doses as soon as possible. Levothyroxine compositions of the present invention may be administered to infants and children who cannot swallow intact tablets by crushing the tablet and suspending the freshly crushed tablet in a small amount (5–10 mL or 1–2 teaspoons) of water. This suspension can be administered by spoon or dropper. Foods that decrease absorption of levothyroxine, such as soybean infant formula, should not be used for administering levothyroxine sodium tablets.

A recommended starting dose of levothyroxine sodium in newborn infants is about 10 to about 15 mcg/kg/day. A lower starting dose (e.g., about 25 mcg/day) may be considered in infants at risk for cardiac failure, and the dose should be increased in 4–6 weeks as needed based on clinical and laboratory response to treatment. In infants with very low (< about 5 mcg/dL) or undetectable serum $T_4$ concentrations, a recommended initial starting dose is about 50 mcg/day of levothyroxine sodium.

As indicated above, levothyroxine therapy is usually initiated at full replacement doses, with the recommended dose per body weightdecreasing with age (see Dose Table below). However, in children with chronic or severe hypothyroidism, an initial dose of about 25 mcg/day of levothyroxine sodium is recommended with increments of 25 mcg every 2–4 weeks until the desired effect is achieved. Hyperactivity in an older child may be minimized if the starting dose is one-fourth of the recommended full replacement dose, and the dose is then increased on a weekly basis by an amount equal to one-fourth the full-recommended replacement dose until the full recommended replacement dose is reached.

Dose Table: Levothyroxine Sodium Dosing Guidelines for Pediatric Hypothyroidism

| AGE | Daily Dose per Kg Body Weight[a] |
|---|---|
| 0–3 months | 10–15 mcg/kg/day |
| 3–6 months | 8–10 mcg/kg/day |
| 6–12 months | 6–8 mcg/kg/day |
| 1–5 years | 5–6 mcg/kg/day |
| 6–12 years | 4–5 mcg/kg/day |
| >12 years | 2–3 mcg/kg/day |
| Growth and puberty complete | 1.7 mcg/kg/day |

[a]The dose should be adjusted based on clinical response and laboratory parameters.

Levothyroxine sodium tablets, USP, in accordance with the present invention may be supplied as oval or violin-shaped, color-coded, potency marked tablets in, for example, 12 strengths, as indicated in the Strength Table below.

Strength Table
Levothyroxine Tablets

| Tablet Strength (mcg) | Tablet Color |
|---|---|
| 25 | Orange |
| 50 | White |
| 75 | Purple |
| 88 | Olive |
| 100 | Yellow |
| 112 | Rose |
| 125 | Brown |
| 137 | Dark Blue |
| 150 | Blue |
| 175 | Turquiose |
| 200 | Pink |
| 300 | Green |

When the parmaceutically active moiety is liothyronine sodium, the preferred amount of the active moiety in the composition is present in the range of about 0.000005 to 0.5 weight %. The more preferred range is from about 0.00001 to 0.1 weight %, and the most preferred range is from about 0.00004 to about 0.002 weight % liothyronine. The minimum amount of lyothyronine can vary, so long as an effective amount is utilized to cause the desired pharmacological effect. Typically, the dosage forms have a content of levothyroxine in the range of about 5 to 50 micrograms per 145 milligram pill for human applications.

The β-form microcrystalline cellulose product of the present invention is prepared by forming a wet cake, drying the cake with a drum dryer, then passing the dried product through a screen or mill for sizing which produces β-sheet microcrystalline cellulose which has a flat needle shape, as disclosed in U.S. Pat. No. 5,574,150. Such β-sheet microcrystalline product is available from Asahi Chemical of Japan and/or marketed by FMC Company of Newark, Del., under the trademark Ceolus®. The morphology and performance characteristics of the Ceolus® product are different from those of α-form microcellulose products (for example, Avicel® and Emcocel®), and are suitable for preparing the present stabilized pharmaceutical composition.

The amount of β-form microcrystalline product used in the present composition is at least 50 weight % of the final composition. Preferably, the amount of β-form microcrystalline product is in the range of about 50 to 99 weight %. Most preferably, the amount of β-form microcrystalline product is in the range of about 60 to 90 weight % of the final composition.

Other suitable excipients for the present invention include fillers such as starch, alkaline inorganic salts, such as trisodium phosphate, tricalcium phosphate, calcium sulfate and sodium or magnesium carbonate. The fillers can be present in the present composition in the range of from about 0 to 50 weight %.

Suitable disintegrating agents include cornstarch, cross-linked sodium carboxymethylcellulose (croscarmellose) and cross-linked polyvinyipyrrolidone (crospovidone). A preferred disintegrating agent is croscarmellose. The amount of disintegrating agent used is in the range of about 0 to 50 weight %. Preferably, the disintegrating agent is in the range of about 5 to 40 weight %, more preferably about 10 to about 30 weight %. This is in substantial excess of the recommended levels of such materials. For example, the recommended loading of croscarmellose is from 0.5 to about 2% by weight. However, it has been found that the higher loadings of the disintegrating agents substantially improves the ability of the product to disperse in aqueous media.

Suitable gildents for use in the present invention include colloidal silicon dioxide and talc. The amount of gildent in the present composition is from about 0 to 5 weight %, and the preferred amount is about 0 to 2.weight %.

Suitable lubricants include magnesium and zinc stearate, sodium stearate fumarate and sodium and magnesium lauryl sulfate. A preferred lubricant is magnesium stearate. The amount of lubricant is typically in the range of about 0 to 5 weight %, preferably in the range of about 0.1 to 3 weight %.

The oral pharmaceutical product is prepared by thoroughly intermixing the active moiety and the β-form of microcrystalline cellulose, along with other excipients to form the oral dosage. Food grade dyes can also be added. For example, it is common to distinguish dosages of various potency by the color characteristics of such dyes.

As discussed, a preferred immediate release pharmaceutical composition in tablet form includes levothyroxine sodium. In a preferred embodiment, the composition includes at least one of, preferably all of the following:

a) between from about 0.01 mg/tablet to about 500 mg/tablet levothyroxine sodium (USP);
b) between from about 100 mg/tablet to about 110 mg/tablet of microcrystalline β-cellulose, NF (Ceolus®) having a bulk density of between from. about 0.10 g/cm$^3$ to about 0.35 g/cm$^3$;
c) between from about 25 mg/tablet to about 50 mg/tablet of croscarmellose sodium, NF (Ac-di-sol®); and
d) between from about 0.5 mg/tablet to about 5 mg/tablet of magnesium stearate, NF.

Preferably, the composition further comprises at least one pharmaceutically acceptable coloring agent.

More particular methods according to the invention provide compositions having less than about 5% total impurities, as determined by the standard impurity test. Preferably, the method further comprises forming a tablet, particularly those tablets having a raised violin configuration.

The stabilized oral dosages of thyroid hormone are prepared by forming a trituration of the active moiety (i.e. levothyroxine sodium and/or liothyronine sodium) and β-form microcrystalline cellulose. The trituration is blended with β-form microcrystalline cellulose and additional excipients and compressed into oral dosages.

Design of the tableting apparatus is important, in order to maintain consistency from one oral dosage to the next. The formulation batches are a blend of solid compositions of various shapes and sizes. Blending is used to achieve a measure of homogeneity. In particular the active thyroid moiety is desired to be evenly distributed throughout the batch. In a typical 410 kg batch, the amount of active moiety represents less than 1 kg of the total weight. For example, when producing 145 mg tablets with a 300 mcg dosage, approximately 0.8 kg of a 410 kg batch is the active moiety. In addition each tablet is formulated to contain 100% label claim potency.

It is typical for compressible medicament tablets to be formed using a 2:1 fill to compression ratio. However, for medicament tablets formed using the present invention a fill to compression ratio from 3.3:1 to 4:1 is needed to obtain desired tablet density. The β-form microcrystalline cellulose has a lower bulk density, as compared to other excipients.

Higher tablet density can be accomplished by adjusting a tableting machine to increase the compression ratio. Tableting machines are commonly known to practitioners in the art and include those available from Manesty and Stokes. It has been found that making such adjustments to the compression ratio results in poor tablet surface finish as well as inconsistent tablet weights. Instead, the design of the tableting dies should be adjusted. It has been determined that during the filling of the tableting dies, a minimum of 5–6 mm die overfill should be used. In most cases, this requires replacement of the usual tableting dies with dies which are an additional 2–3 mm deep.

When using the extra-deep dies and a compression ratio of from 3.3:1 to 4.0:1, consistent weight tablets with good surface finish were produced.

Figure 1C:
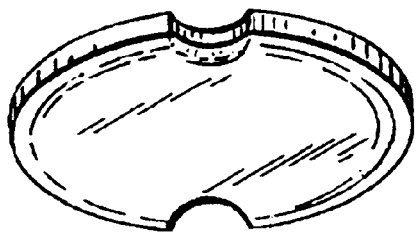
Figure 2:
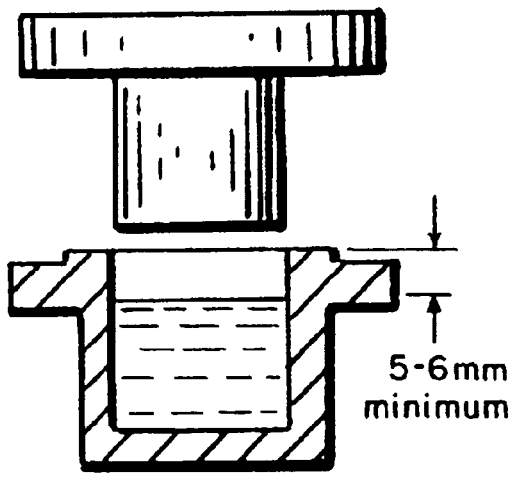
FIG. 2 illustrates a tableting die pair.
Figure 3:
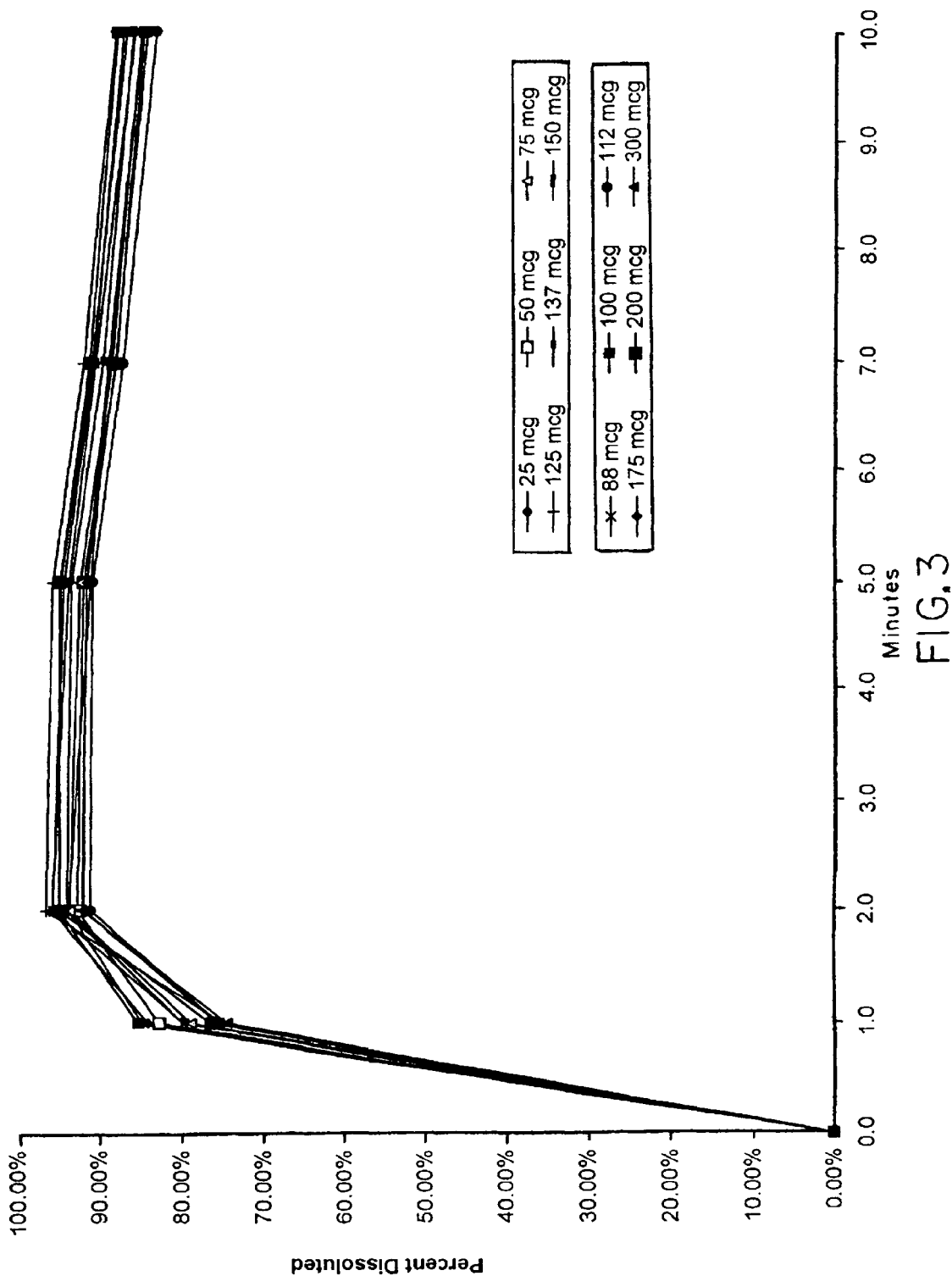
FIG. 3 is a graphical depiction of comparative dissolution data of various strengths of Levoxyt® tablets made in accordance with the invention.

Preferably, the shape of the tablet is configured to increase heat transfer away from the tablet. More preferred tablets have a surface area per tablet of between from about 0.9 in.$^2$ to about 0.15 in.$^2$, preferably about 0.115 in.$^2$, to assist such heat transfer. Additional tablet configurations are contemplated e.g., tablets that are beveled and/or include a notch. A preferred tablet shape is a raised violin configuration, as shown in FIG. 1C.

The following examples are given by way of illustration only and are not to be considered limitations of this invention or many apparent variations of which are possible without departing from the spirit or scope thereof.

EXAMPLE 1

Stability Tests

Stability testing was performed on samples of the thyroid hormone drug formulation used in manufacturing tablets with an active moiety of levothyroxine sodium. Tests were performed on direct compression formulations for the dosage strength of 25 mcg. Example 1 tablets comprise the β-form microcrystalline cellulose while Control 1 tablets comprise the traditional β-form microcrystalline cellulose. The composition of Example 1 and Control 1 tablets are presented in Table 1 and stability test results in Table 2 below.

TABLE 1

Tablet Formulation for 25 mcg Dosages of Levothyroxine Sodium

| Example 1 Tablet | Control 1 Tablet | Component |
| --- | --- | --- |
| 0.0297 mg | 0.0297 mg | Levothyroxine Sodium, USP |
| 108.55 mg | — | β-sheet microcrystalline cellulose |
| — | 108.55 mg | α-form microcrystalline cellulose |
| 35.079 mg | 35.079 mg | croscarmellose Sodium, NF |
| 0.352 mg | 0.352 mg | FD&C Yellow #6 16% (14–20% |
| 1.018 mg | 1.018 mg | Magnesium Stearate, NF |
| 145.0 mg | 145.0 mg | Total |

TABLE 2

Stability Test-Potency at 25° C.-% Label Claim

| Elapsed Time | 0 | 73 Days | 13 months | 5 months |
| --- | --- | --- | --- | --- |
| Example 1 Tablet | 106.4 | 105.5 | 104.4 | 102.9 |
| Example 1% Potency Loss | 0.0 | 0.9% | 2.0% | 3.5% |
| % Change per Month | 0.0 | 0.37 | 0.15 | 0.23 |
| Control 1 Tablet | 99.2 | 89.5 | 85.0 | 83.2 |
| Control 1% Potency Loss | 0.0 | 2.7% | 14.2% | 16.0% |
| % Change per Month | 0.0 | 1.11 | 1.09 | 1.07 |

As seen in Table 2, the stability of pharmaceutical formulations of the present invention is improved significantly by the use of the β-sheet microcrystalline cellulose. Potency loss of the present invention after 15 months is 3.5%, versus 16.0% potency loss experienced in a similar formulation with the α-form microcrystalline cellulose. The average loss in potency per month in the case of the compositions of the present invention was only about 0.2% per month, as compared to over 1% per month for the T4 products which included β-form microcrystalline cellulose, thus demonstrating a stability which is about 3 to 4 times better than the T4 products which utilized α-form microcrystalline cellulose.

Tableting testing was performed on the formulation for Example 1 tablets. Initial results with standard die depths provided a relative standard deviation of 2.2 to 3.5% tablet weight. With the use of the herein described extra deep tablet dies, the relative standard deviation is 1.2%. Testing was performed on a Manesty tableting machine with compression ratios of from 3.3:1 to 4.0:1.

Tablet quality is also dependent upon the storage of the β-sheet microcrystalline cellulose. Best results are achieved when the cellulose is received in drums or portable containers instead of bags. The bag form suffers from compression during transportation from raw material suppliers. Test results for tableting are presented in attached Exhibit A.

Additional examples of solid dosage formulations are illustrated in Tables 3 and 4. Stability testing data of additional examples are illustrated in Table 5.

TABLE 3

Tablet Formulation for Dosages of Levothyroxine Sodium (per tablet)

| 25 mcg Dosage | 50 mcg Dosage | 75 mcg Dosage | Component |
| --- | --- | --- | --- |
| 0.025 mg | 0.0500 mg | 0.0750 mg | levothyroxine sodium |
| 108.529 mg | 108.856 mg | 108.438 mg | β-form microcrystalline cellulose |
| 35.079 mg | 35.079 mg | 35.079 mg | croscarmellose sodium |
| 0.352 mg | | 0.383 mg | food grade dye |
| 1.018 mg | 1.018 mg | 1.018 mg | magnesium stearate |
| 145 mg/tablet | 145 mg/tablet | 145 mg/tablet | Total |

TABLE 4

Tablet Formulation for Dosages of Levothyroxine Sodium (per tablet)

| 100 mcg Dosage | 112 mcg Dosage | 300 mcg Dosage | Component |
| --- | --- | --- | --- |
| 0.100 mg | 0.112 mg | 0.300 mg | Levothyroxine sodium |
| 108.406 mg | 107.711 mg | 108.451 mg | β-form microcrystalline cellulose |
| 35.079 mg | 35.079 mg | 35.079 mg | croscarmellose |
| 0.388 mg | 1.080 mg | 0.142 mg | food grade dye |
| 1.018 mg | 1.018 mg | 1.1018 mg | magnesium stearate |
| 145 mg/tablet | 145 mg/tablet | 145 mg/tablet | Total |

Table 5 shows drug stability data for a number of the above formulations.

TABLE 5

Stability Test-Potency at 25° C.-% Label Claim

| Levothyroxine Na Test | Test Interval (months) | | | |
|---|---|---|---|---|
| | Initi | 6 | 12 | 18 |
| 25 μg Dose | 26.2 | 25.6 | 25.5 | 25.3 |
| % Label Claim | 104. | 102. | 102. | 101. |
| % of Initial Result | 100. | 97.5 | 97.3 | 96.6 |
| % Change | 0.0 | 2.6 | 2.8 | 3.6 |
| % Change per month | 0.0 | 0.43 | 0.23 | 0.2 |
| 50 μG Dose | 51.0 | 49.9 | 48.9 | 48.4 |
| % Label Claim | 102. | 99.7 | 97.7 | 96.7 |
| % of Initial Result | 100. | 97.7 | 95.8 | 94.8 |
| % Change | 0.0 | 2.3 | 4.3 | 5.3 |
| % Change per month | 0.0 | 0.38 | 0.36 | 0.29 |
| 112 μg Dose | 113. | 113. | 109. | 105. |
| % Label Claim | 101. | 101. | 97.8 | 94.5 |
| % of Initial Result | 100. | 100. | 96.6 | 93.4 |
| % Change | 0.0 | 0.3 | 3.4 | 6.7 |
| % Change per month | 0.0 | 0.05 | 0.28 | 0.37 |
| 200 μg Dose | 202. | 196. | 198. | 196. |

TABLE 5-continued

Stability Test-Potency at 25° C.-% Label Claim

| Levothyroxine Na Test | Test Interval (months) | | | |
|---|---|---|---|---|
| | Initi | 6 | 12 | 18 |
| % Label Claim | 101. | 98.4 | 99.3 | 98.3 |
| % of Initial Result | 100. | 97.3 | 98.2 | 97.2 |
| % Change | 0.0 | 2.7 | 1.7 | 2.8 |
| % Change per month | 0.0 | 0.45 | 0.14 | 0.15 |

Thus the formulations of the present invention provide extreme stability for the levothyroxine activity over an extended shelf life for these pharmaceutical products.

EXAMPLE 2

Dissolution Tests

The following preferred method for testing potency will sometimes be referred to herein as method number: AM-004B.

TABLE 6

Dissolution Test Procedure

| | |
|---|---|
| Chromatographic Conditions | |
| Mobile Phase: | Degassed and filtered mixture of methanol and 0.1% phosphoric acid (60:40). |
| Column: | $C_{18}$ 3.9 mm × 30 cm |
| Flow Rate: | 2.0 ml/minute |
| Detector: | Deuterium set at 225 nm |
| Injection Volume: | 800 μL |
| System Suitability: | Chromatograph 6 replicate injections of the standard preparation. 1.0 RDS for the standard replicates must not be more than 4.0%. 2.0 The tailing factor must not be more than 1.5. |
| Medium: | 0.01 N hydrochloric acid containing 0.2% sodium lauryl sulfate; 500 ± 5 ml; 37 ± 0.5° C. This solution is very foamy; excessive mixing, shaking, and pouring will make reading the meniscus on the graduated cylinder difficult. |
| Apparatus: | Apparatus 2 (Paddles) |
| Apparatus Cleaning: | The apparatus is to be cleaned immediately after use or if left idle for more than 12 hours. Clean paddles by rinsing with distilled water, methanol, and distilled water again. Blot to dry with Kimwipes. Clean vessels by rinsing with hot tap water, microdetergent, hot tap water, and distilled water. Dry using paper towels. |
| Paddle Speed: | 50 rpm |
| Incubation Period: | Up to 45 minutes |
| Standard Solutions: | Transfer about 50 mg USP Levothyroxine RS, accurately weighed, into a 100 ml volumetric flask. Add approximately 30 ml of methanol, dissolve and dilute to volume with methanol, mix. Using this solution, standard solutions are prepared in a volumetric flask using Dissolution Media, diluting to a concentration that comes near to the theoretical concentration of the tablet in 500 ml of Dissolution Media. Use a pipette to gently add the Dissolution media to prevent foaming. *Calculate and use the actual concentration in % Dissoluted equation |
| Sample Preparation: | One tablet is placed into each vessel of the dissolution apparatus. Sample each vessel after the incubation time, as stated above. Pass a portion of the sample through a 0.45 micron filter sufficient to equilibrate the filer. Filters are to be pre-qualified according to SOP (C1-730). Use a new filter for each vessel. |
| Procedure: | Inject 800 μl of standard and sample into the column and record the chromatograms. Measure the responses of the major peaks. Calculate the amount of Levothyroxine dissolved in each vessel by the formula below. |

Calculations: % Dissoluted = (Sample Area / Std. Area) × (798.86 / 776.87) × (Amt. Std. Injected / Amt. Samp. Injected) × 100% = % Dissoluted Where
  798.86=molecular weight of Levothyroxine as Sodium Salt
  776.87=molecular weight of Levothyroxine (as Base)

TABLE 7

Acceptance Criteria

| STAGE | #TESTED | ACCEPTANCE CRITERIA Q = 70% |
|---|---|---|
| S-1 | 6 | Each unit is not less than Q + 5% |
| S-2 | 6 | Average of 12 units (S-1 + S-2) is equal to or greater than Q, and no unit is less than Q-15% |
| S-3 | 12 | Average of 24 units (S-1 + S-2 + S-3) is equal to or greater than Q and not more than 2 units are less than Q-15%, and no unit is less than Q-25% |

Table 8 shows comparative dissolution data for all strengths of Levoxyl® tablets.

TABLE 8

Comparative Dissolution Data

| | 0 minutes | 1 minute | 2.5 minute | 5 minutes | 7.5 minutes | 10 minutes |
|---|---|---|---|---|---|---|
| 25 mcg | 0.0% | 84.9% | 93.7% | 90.9% | 88.6% | 84.7% |
| 50 mcg | 0.0% | 82.8% | 92.7% | 91.8% | 87.8% | 84.4% |
| 75 mcg | 0.0% | 78.9% | 93.6% | 92.2% | 88.3% | 84.7% |
| 88 mcg | 0.0% | 79.8% | 95.6% | 94.1% | 90.5% | 86.9% |
| 100 mcg | 0.0% | 85.4% | 94.8% | 94.5% | 90.7% | 86.5% |
| 112 mcg | 0.0% | 75.5% | 91.1% | 90.7% | 87.0% | 82.9% |
| 125 mcg | 0.0% | 75.0% | 96.5% | 95.5% | 91.7% | 87.8% |
| 137 mcg | 0.0% | 79.9% | 93.9% | 93.2% | 89.4% | 85.7% |
| 150 mcg | 0.0% | 75.6% | 91.9% | 91.4% | 88.7% | 84.6% |
| 175 mcg | 0.0% | 84.2% | 95.7% | 93.5% | 90.3% | 85.5% |
| 200 mcg | 0.0% | 76.5% | 94.9% | 94.6% | 91.0% | 87.6% |
| 300 mcg | 0.0% | 74.5% | 92.1% | 91.4% | 87.9% | 84.0% |

Figure 4A:
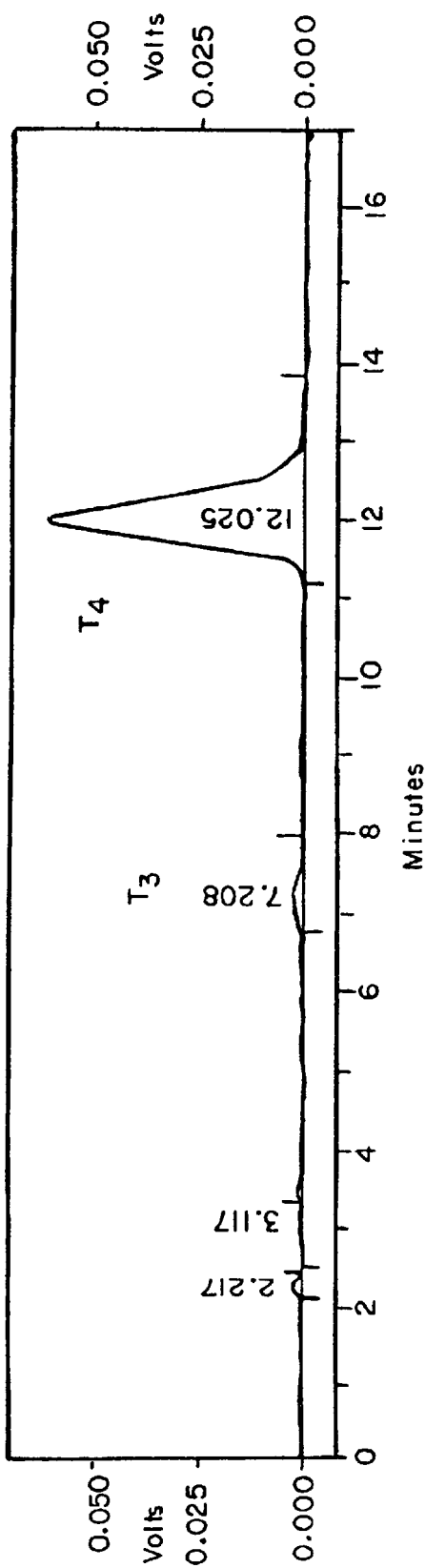
FIG. 4A is an HPLC chromatogram showing levothryoxine and liothronine standards.
Figure 4B:
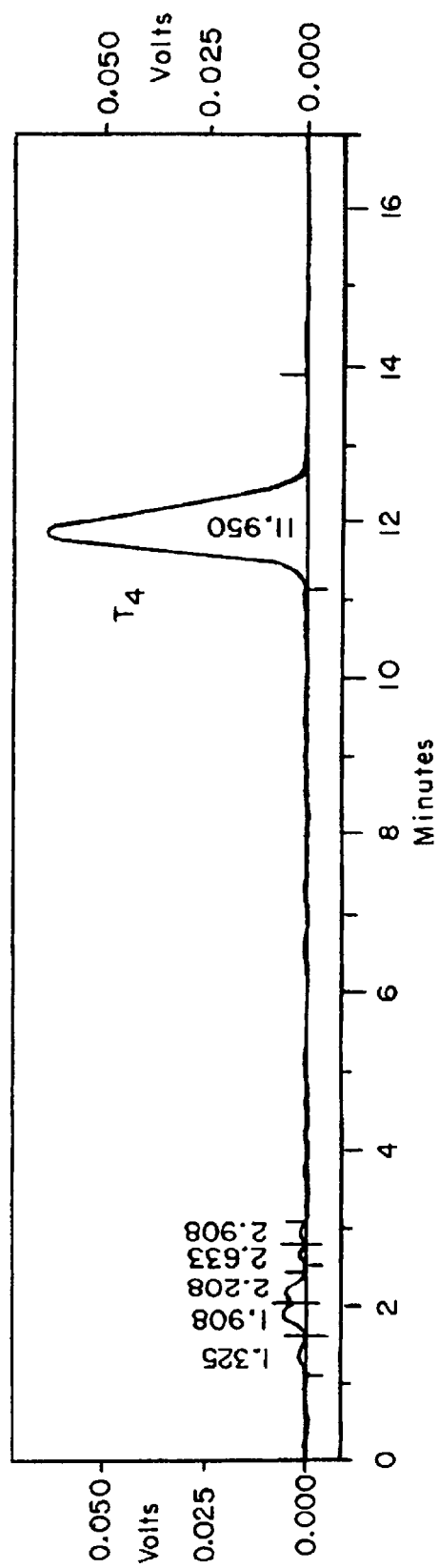
FIG. 4B is an HPLC chromatograph showing results of a levothyroxine sodium sample made in accordance with the present invention.

FIG. 4 depicts graphs showing the mean results for each of the tablet strengths of Levoxyl® tested. Each point is the mean of three dissolutions, testing 12 tablets per dissolution or n=36. The data is presented as percent of label claim dissoluted vs. dissolution time.

The results demonstrate that the multi-point dissolution profiles for Levoxyl® tablets are similar across a wide variety of tablet strengths. Moreover, all strengths substantially exceed the requirements for immediate release oral dosage forms (i.e. at least 80% dissoluted with 15–20 minutes). In each dosage form, these pills were over 90% dissoluted within two and a half minutes.

The extremely rapid dispersion rates for the tablets of the present invention make possible a simplified treatment method for infants or others who have difficulty swallowing pills. In this approach, the appropriate dosage for the patient in question, in an immediate release pill made in accordance with the present invention, is simply mixed with a suitable amount, e.g. 50–200 ml, of aqueous fluid, such as water, soft drinks, juice, milk, etc. The immediate release pill is easily dissolved in the fluid, optionally with stirring or shaking, and simply administered to the patient.

EXAMPLE 3

Potency Test

The following method for testing potency of the tablets will sometimes be referred to herein as method number: AM-003. Alternatively, the tablet potency can be tested according to method AM-021. Method number: AM-021 is the same as method number: AM-003, except the tablets are dissolved whole without first grinding the tablets into a powder, as with method number: AM-003.

Method Reference:
  USP 24 pp. 968–970.
Chromatographic Conditions:
  Mobile Phase: 65:35:0.05 H20: CAN: H3P04 degassed and filtered; mobile phase composition may be altered to achieve a satisfactory resolution factor.
Column:
  ACN, 4.6 mm×25 to 30 cm.
Flow Rate:
  1.5 ml/minute.
Detector:
  Deuterium, set at 225 nm.
Injection Volume:
  100 ml.
System Suitability:
  Chromatograph 5 replicate injections of the standard preparation. Record the peak responses as directed under "Procedure".
  1.0 RSD for the standard replicates must not be more than 2.0% for $T_4$.
  2.0 Calculate the resolution factor R on one of the five replicates. The R-value must be greater than or equal to 5.0 to proceed. See Method QC-009.
Standard Preparation:
  Accurately weigh 25 mg of USP Levothyroxine RS and transfer to an amber 250-ml volumetric flask. Add approximately 50 ml extraction mobile phase. Let stand for 20 minutes with occasional swirling. Sonicate for 30 seconds. Gradually add more extraction solution and repeat sonication until no undissolved particles are observed. Dilute to volume with extraction solution. Mix well. The concentration of $T_4$ is about 100 µg/ml. Also dissolve an accurately weighed quantity of USP Liothyronine RS to yield about 100 mg/ml, done as above with USP Levothyroxine RS. Label this solution as stock $T_3$-A.
Stock Standard Dilution:
  1. Pipette 10.0 ml stock $T_3$-A into a 500 ml Type A volumetric flask.
  2. Dilute to volume with Mobile Phase for a concentration of about 2 µg/ml. Mix well and label this solution as std. $T_3$-B.
  3. Pipette 50.0 ml each from the $T_4$ and $T_3$-B stock standards and transfer into a 500-ml Type A volumetric flask.
  Dilute to volume with mobile phase and mix well. Label this standard as $T_3/T_4$ working standard. The concentration of the working standard should be about 0.2 µg/ml $T_3$ and 10.0 µg/ml $T_4$.
Note:
  Concentrations of Levothyroxine and Liothyronine require adjustments for water content.
Assay Preparation:
  Weigh not less than the specified tablet quantity and calculate the average tablet weight. Crush tablets into a uniform fine powder with a mortar and pestle. Tare a polypropylene weigh boat.

Accurately weigh (to 0.1 mg) a portion of the powder into the tared weigh boat using a preconditioned stainless steel scoop or spatula (either Teflon coated or uncoated). The spatula or scoop is preconditioned by dipping it into the powder. Use the Sample Calculation below to achieve 50 ml of a 10 µg/ml assay solution.

Record the sample weight taken. Carefully transfer the sample into an Erlenmeyer flask, reweigh the weigh boat and subtract the residual weight from the weight taken to obtain the actual sample weight. Pipette 50 ml of mobile phase into the flask. Cover the flask with parafilm, sonicate for approximately 10 seconds and vortex for approximately 235 seconds at a speed of 6 or greater. Observe sample preparation, and if clumping is noted, repeat the sonication and/or vortex steps. Centrifuge (~3,000 rpm) for NLT 1 minute until a clear supernatant is achieved. Transfer a portion of the supernatant to an auto sampler vial.

For In-Process granulation analysis, use the theoretical tablet weight (0.1455 g) in place of (weight of tablets/number of tablets) in the formula below.

Sample Calculation:

$$\frac{\text{Weight of Tablets}}{\text{Number of Tablets}} \times 10 \text{ µg/ml} \times \frac{50 \text{ ml}}{\text{Dose (µg)}} = \text{Amount to Weight Out per Assay}$$

Procedure:

Separately inject 100 µl of the sample onto the column. Record the responses of the analyte peak and calculate % label claim as follows.

Calculations:

Sample Area×Std conc. (µg)×50 ml×avg. tablet weight in g×798.86=µg/dose×100=% Label Claim Standard Area (ml) Actual Sample wt in g 776.87 Label Claim Where 798.86=molecular weight of Levothyroxine as the Sodium Salt 776.87=molecular weight of Levothyroxine Standard Base Results:

FIGS. 5A and 5B show HPLC chromatograms of levothyroxine and liothyronine controls (T3/T4 working standard, shown in FIG. 5A) and an experimental sample made in accordance with the present invention as described above (FIG. 5B). The peaks in both chromatograms in the area of 1.325 to 3.1 correspond to materials in the solvent. The peak at about 7.2 in FIG. 5A shows the presence of T3. FIG. 5B shows the absence of T3, as well as the absence of other related products or degradation products of levothyroxine.

EXAMPLE 4

Hardness Test

The following preferred method for testing tablet hardness will sometimes be referred to herein as method number: QC-005.

TABLE 9

QC-005 Hardness Test Procedure

| | |
|---|---|
| APPARATUS: | Van-Keel hardness tester; Please refer to equipment Profile for instrument information. |
| PROCEDURE: | Lay the tablet flat with the score side up onto the instrument in between the jaw area. The tablet's score line should be perpendicular to the jaw's line for the tablet to be aligned properly. Refer to alignment diagram below. For Tamil-K caplets, place the caplet onto the instrument on its side. The caplet's score line should not be laying on the flat part of the testing area as with other tablets but should not be parallel to the jaw's line for the caplet to be aligned properly. Refer to alignment diagram below. Push the test button on the control panel. The jaws will automatically move the break the tablet. The force needed to break the tablet (KP) will read out on the digital display and print out on the print tape. Specifications: 6.0–14.0 kiloponds |
| RESULTS: | Typical results range from about 9.3 to about 12.3 kiloponds. |

Generally the hardness of the pills lies between about 6.0 and about 14.0 kiloponds. Preferably the pill hardness is from about 9 to about 13 kiloponds. Typical results of products made in accordance with the present invention are about 9.3, 11.3, 9.8, 10.2, 12.3, etc. Pharmaceutical tablets which incorporate granulated active ingredient are typically much higher in hardness, which may add to the difficulty of dissolving or dissoluting them. Pills which are lower in hardness generally present more problems of pill fragmentation during handling and storage.

EXAMPLE 5

Impurity Tests

The following preferred method for testing tablet impurities is sometimes referenced herein as method number: SA-004.

TABLE 10

SA 004 Impurity Test Procedure

| | |
|---|---|
| Method Reference: | Biochemie Method No. 1417-6, Report JMI-DP-002 |
| Equipment: | HPLC with a gradient system and a detector at a wavelength of 225 nm |
| Reagents: | Acetonitrile, HPLC grade |
| | Methanol, HPLC grade |
| | Water, HPLC grade |
| | Sodium Hydroxide, ACS reagent grade |
| | Sodium Hydroxide 0.1 solution: Dissolve 40 g of NaOH pellets in 1000 ml HPLC grade water. Store in a plastic container. |
| | Phosphoric acid, 85% reagent grade |
| | Diiodothyronine reference material |

TABLE 10-continued

SA 004 Impurity Test Procedure

| | |
|---|---|
| | Liothyronine RS USP reference material |
| | Levothyroxine RS USP reference material |
| | Triiodothyroacetic acid reference material |
| | Tetraiodothyroacetic acid reference material |
| | Solvent 1: To 100.0 ml of 0.1 N Sodium Hydroxide solution add a 1:1 V/V mixture of methanol and water to make 1000 ml. |
| | Solvent 2: 77:23:0.1 H2): CANACN: H3PO4; Degassed and filtered; mobile phase composition a may be altered to achieve a satisfactory resolution factor. |
| | Extraction solution: Pipette 50 ml of solvent 1 into a 1000 ml volumetric flask dilute to volume with solvent 2, stopper and mix well. |
| Chromatography Column: | Nucleosil 100-10CN, 250 mm long, 4.6 mm internal diameter, at ambient temperature |
| System: | Gradient Elution |
| | Mobile phase A: 1000: 1 H2O:H3PO4 V/V |
| | Mobile phase B: Acetonitrile |
| | Gradient program: |
| | Time |
| | min |
| | % of mobile phase A |
| | % of mobile phase B |
| | 0 |
| | 77 |
| | 23 |
| | 13 |
| | 77 |
| | 23 |
| | 15 |
| | 65 |
| | 35 |
| | 24 |
| | 65 |
| | 35 |
| | 26 |
| | 77 |
| | 23 |
| | Flow rate: 1.5 ml/min. |
| | Injection Volume: 100 up: next injection after approx. 40 min. |
| | Detector: UV, 225 nm |
| System Suitability: | Chromatograph 5 replicate injections of the Reference I Standard preparation, chromatograph 2 replicate injections of the Reference II Standard. Record the peak responses as directed under "Procedure". An extraction blank is to be run after the standards. |
| | 1. The RSD must not be greater than 2.0% for each of the impurities in the standard reference solution I. |
| | 2. The resolution factor between liothyronine and levothyroxine in the standard reference solution I must not be less than 5.0. |
| | 3. The Signal to Noise ratio must not be less than 5/1 for levothyroxine and impurities in the chromatogram obtained with standard reference solution II. |
| | 4. A peak of monochlorotriiodothyronine may occur just before the levothyroxine peak. Make sure that the degree of separation between this peak and of levothyroxine is at least sufficient to permit separate evaluations. Monochlorotriiodothyronine reference material is not available to be purchase by any vendor. Any calculation of monochlorotriiodothyronine impurity will be done by its retention time. |
| Standards Preparation: | 1. Stock Standard Reference Solution: Accurately weigh 10 mg +/− 0.1 mg of each Diiodothyronine, Liothyronine, Levothyroxine, Triiodothyroacetic acid and Tetraiodthyroacetic acid reference standards into a 100 ml volumetric flask. Dissolve in Solvent 1 and dilute to volume, stopper and mix well. The concentration of each component will be approximately 100 mcg/mlL. |
| | 2. Standard Reference solution I: Pipette 5.0 ml of Stock Standard Reference Solution into a 100 ml volumetric flask, dilute to volume with Solvent 2, stopper and mix well. The Final concentration of each component will be approximately 5 mcg/mlL. |
| | 3. Standard Reference solution II (0.05%): Pipette 2.0 ml of Standard Reference Solution I into a 100 ml volumetric flask, dilute to volume with Solvent 2, stopper and mix well. The final concentration of each component will be approximately 0.1 mcg/mlL. 100 |
| Test Preparation: | Crush not less than 20 tablets. Tare a 250 ml Erlenmeyer flask. Accurately weigh to the nearest 0.1 mg an equivalent of 500 mcg of levothyroxine sodium (+/−10%) into a 250 ml Erlenmeyer flask. Pipette 100.0 mcg of the Extraction solution into the flask cover the flask with parafilm, sonicate, vortex and then centrifuge the solution for 1 minute each. The final concentration of the |

TABLE 10-continued

SA 004 Impurity Test Procedure sample will be approximately 5 mcg/ml of levothyroxine.
To calculate the amount to weigh for the test preparation use the following equation:

$$\frac{500 \text{ mcg} \times 0.1450 \text{ g}^*}{\text{tablet label claim (mcg)}} = \text{Amount to weight for the test prep}$$

*where 0.1450 g = theoretical tablet weight

Note: Analyst must keep all materials use in performing this assay until the results are calculated, checked, and recorded and it is verified that the test is acceptable. This includes the crush, the Erlenmeyer flask with Extraction solution, the centrifuge tube and the auto-sampler vial. If the analysis is running overnight, these materials should be sealed with parafilm and saved until results are obtained and the results are deemed acceptable.

Procedure:
1. Separately inject 100 μl of the sample preparation onto the column. Record the response of the analyte peaks and the calculate % w/w using the equations below.
2. The chromatogram may need to be reprocessed to obtain optimal integration. A copy of the sample chromatograph is to be attached to the analytical packet.
3. Peaks on the sample chromatograph with areas less than a signal ratio of 5/1 will be considered none detected.

Calculations:
Diiodothyronine:

Sample $$\frac{\text{Sample area}}{\text{Std. Area}} \times \text{Std. conc.} \frac{(\text{mcg})}{\text{ml}} \times \frac{100 \text{ ml}}{\text{Wsimpl (g)}} \times \frac{100\%}{1000000 \text{ mcg/g}} \times 1.11^* = \% \text{ w/w}$$

or

Sample area × Std. Conc. (mcg) × 0.01 × 1.11* = % w/w

*where 1.11 is a correction factor

Triiodothyroacetic Acid:

$$\frac{\text{Sample area}}{\text{Std. Area}} \times \text{Std conc.} \frac{(\text{mcg})}{\text{ml}} \times \frac{100 \text{ ml}}{\text{Wsimpl (g)}} \times \frac{100\%}{1000000 \text{ mcg/g}} = \% \text{ w/w}$$

or $$\frac{\text{Sample area}}{\text{Std. Area}} \times \text{Std Conc.} \frac{(\text{mcg})}{\text{ml}} \times \frac{0.01}{\text{Wsimpl (g)}} = \% \text{ w/w}$$

Tetraiodothyroacetic Acid:

Sample $$\frac{\text{Sample area}}{\text{Std. Area}} \times \text{Std. conc.} \frac{(\text{mcg})}{\text{ml}} \times \frac{100 \text{ ml}}{\text{Wsimpl (g)}} \times \frac{100\%}{1000000 \text{ mcg/g}} \times 1.16^* = \% \text{ w/w}$$

or $$\frac{\text{Sample area}}{\text{Std area}} \times \text{Std Conc.} \frac{(\text{mcg})}{\text{ml}} \times \frac{0.01}{\text{Wsimpl (g)}} \times 1.16^* = \% \text{ w/w}$$

*where 1.16 is a correction factor

Limit of Detection (LOD) Values

| Impurity | Limit of Detection |
|---|---|
| Diiodothyronine (T2) | 0.00625% |
| Triiodothyroacetic Acid (Reverse T3) | 0.003125% |
| Tetraiodothyroacetic Acid (Reverse T4) | 0.003125% |

Calculation of the theoretical area for 0.05% of levothyroxine sodium, based on the initial amount in mg of levathyroxine sodium in the whole sample weight.

$$\frac{(Area\, rs\, II)(A)(10.0)}{(.05)(T_4 std\, st.)(P)(1.0283)} =$$

Theoretical area for 0.05% of levothyroxine Na, based on the actual weight

Where:

Area$_{rs}\pi$—is the average area of the levothyroxine in the Standard reference solution II A=is the initial weight of levothyroxine Na in mg represented by the sample weight.

This is calculated by using this equation: =

$$\frac{sample\ weight\ (g) \times claim\ T_4\ in\ mcg}{0.1450\ g \times 1000\ mcg/mg}$$

10.0=theoretical initial weight of the Levothyroxine USP reference standard 0.500=is the theoretical initial weight of the Levothyroxine NA to be tested, in mg T$_4$ std. Wt.=the initial weight of the levothyroxine USP standard in mg P=the purity of the levothyroxine Na USP standard (%purity/100%)

1.0283=conversion of levothyroxine into levothyroxine sodium

Greatest unknown impurity (individually):

$$\frac{(Area_{impurity})(T_4 std\ wt\ mg)(1.0283)(P)(100)}{(Area\ ref\ std\ I)(A)(2000)} = impurity\ (\%)$$

Where:

Area$_{impurity}$ is the area of the greatest unknown impurity in the test solution with an area greater than the theoretical area for 0.05% of the levothyroxine Na taken into account.

1.0283=conversion of levothyroxine into levothyroxine sodium.

P=the purity of the levothyroxine Na USP standard (% purity/100%).

100 is the dilution of the test solution.

Area ref std I is the area of the levothyroxine in the standard reference solution I.

A=is the initial weight of levothyroxine Na in mg represented by the sample weight.

This is calculated by using this equation: =

$$\frac{sample\ weight\ (g) \times claim\ T4\ in\ mcg}{0.1450\ g \times 1000\ mcg/mg}$$

2000 is the dilution of the reference solution.

Total of other Unknown Impurities:

$$\frac{(Sum\ area\ impurities)(T4\ std\ wt\ mg)(1.0283)(P)(100)}{(are\ ref\ std\ I)(A)(2000)} =$$

Total Unknown impurities (%)

Where:

Sum area impurity is the sum of the areas of all the other unknown impurities in the test solution (only areas that are greater than the theoretical area for 0.05% of the levothryoxine sodium taken into account).

T4 std. wt.=the initial weight of the levothyroxine USP standard in mg.

1.0283=conversion of levothyroxine into levothyroxine sodium.

P=the purity of the levothyroxine Na USP standard (% pursity/100%).

100 is the dilution of the test solution.

Area ref std I is the area of the levothyroxine in the standard reference solution I.

A=is the initial weight of levothyroxine Na in mg represented by the sample weight.

This is calculated by using this equation: =

$$\frac{sample\ weight\ (g) \times claim\ T4\ in\ mcg}{0.1450\ g \times 100\ mcg/mg}$$

2000 is the dilution of the reference solution.

Results of the test are shown in FIGS. 6A and 6B. FIG. 6A shows an example of a chromatogram of Standard Reference Solution II, with exemplary peaks at about 5.4 for diiodo-1-thyronine, 8.4 for liothryonine, 12.8 for levothyroxine, 19.3 for triiodo thyroacetic acid, and 21.9 for tetraiodo thyroacetic acid. FIG. 6B shows results of an experimental sample of levothyroxine sodium, made in accordance with this invention. As can be seen, the sample had substantially only levothyroxine, with insignificant impurities.

EXAMPLE 6

Liothyronine (T3) Tests

The following preferred method for testing for Triiodothyronine is sometimes referenced herein as method number: QC-001.

TABLE 11

| QC - 001 T3 Test Procedure | |
|---|---|
| Method Reference | USP 24 p. 968–970 |
| Chromatographic Conditions: Mobile Phase: | 65:35:0.05 H$_2$O:CACN:H$_3$PO$_4$ degassed and filtered; mobile phase composition may be altered to achieve a satisfactory resolution factor. |
| Column: | CN, 4.6 mm × 25 to 30 cm |
| Flow Rate: | 2.0 minute/minute |
| Detector: | Deuterium, set at 225 nm |
| Injection Volume: | 100 μL |
| System Suitability: | Chromatograph 5 replicate injections of the standard preparation. Record the peak responses as directed under "Procedure". |
| | 1.0 RSD for the standard replicates must not be more than 2.0% for T$_4$ |

TABLE 11-continued

QC - 001 T3 Test Procedure

| | |
|---|---|
| | 2.0 Calculate the resolution factor (R) on one of the five replicates. The R value must be greater than or equal to proceed. See Method QC-009. |
| Standard Preparation: | Accurately weigh 25 mg of USP Levothyroxine RS and transfer to a clear 250-mlL volumetric flask. Pipette 87.5 ml minute of acetonitrile in the flask. Swirl and then sonicate for less than a minute. Add portions of HPLC grade water to the flask with swirling and sonicating until the material has gone into solution. Be sure that there is no particulate material present. Do not dilute to volume at this point. The solution may be cold. Place into a room temperature water bath for ten minutes to allow the sample to warm to ambient temperature. Dilute to volume with HPLC grade water. Mix well. Label this solution as stock $T_4$ The concentration of $T_4$ is about 100 μg/ml. Also dissolve an accurately weighed quantity of USP Liothyronine RS to yield about 100 μg/minute, done as above with USP Levothyroxine RS. Label this solution as stock $T_3$ -A. Stock Standard dilution: <br> 1. Pipette 10.0 ml stock $T_3$-A into a 500-mlL Type A volumetric flask. <br> 2. Dilute to volume with Mobile Phase for a concentration of about 2 μg/ml. Mix well and label this solution as stock std. c-B. <br> 3. Pipette 50.0 ml each from the $T_4$ and $T_3$ stock standards and transfer into 500-mlL Type A volumetric flask. <br> Dilute to volume with mobile phase and mix well. Label this standard as $T_3/T_4$ working standard. The concentration of the working standard should be about 0.2 μg/ml $T_3$ and 10.0 μg/ml $T_4$. |
| Assay Preparation: | Weigh and crush not less than the specified tablet quantity and calculate the average tablet weight. Tare a polypropylene weigh boat. Accurately weigh (to 0.1 mg) a portion of the powder into the tared weigh boat using a preconditioned stainless steel scoop or spatula (either Teflon coated or uncoated). The spatula or scoop is preconditioned by dipping it into the power. Use the Sample Calculation below to achieve 50 ml of a 10 μg/ml assay solution. Record the sample weight taken. Carefully transfer the sample into an Erlenmeyer flask, reweigh the weigh boat and subtract the residual weight from the weight taken to obtain the actual sample weight. Pipette 50 ml of mobile phase into the flask. Cover the flask with parafilm, sonicate for approximately 10 seconds and vortex for approximately 35 seconds at a speed of 6 or greater. Observe sample preparation, and if clumping is noted, repeat the sonication and/or vortex steps. Centrifuge (~3,000 rpm) for NLT 1 minute until a clear supernatant is achieved. Transfer a portion of the supernatant to an autosampler vial. For In-Process granulation analysis, use the theoretical tablet weight (0.1455 g) in place of (weight of tablets/number of tablets) in the formula below. |
| Note | Analyst must keep all materials used in performing this assay until the results are calculated, checked, and recorded, and it is verified that the test is acceptable. This includes the crush, the Erlenmeyer flask with Mobile Phase, the centrifuge tube and the autosampler vial. If the analysis is running overnight, these materials should be sealed with parafilm and saved until results are obtained and the result is deemed acceptable. |
| Sample Calculation: | $\dfrac{\text{Weight of Tablets}}{\text{Number of Tablets}} \times 10 \ \mu g/ml \times \dfrac{50 \ ml}{\text{Dose } (\mu g)} = \dfrac{\text{Amount to Weigh}}{\text{Out per Assay}}$ |
| Procedure: | Separately inject 100 μl of the sample onto the column. Record the responses of the analyte peak. |
| Calculations: | Calculate the content of liothyronine using the following formula: |

$$\dfrac{\text{Sample} \ T_3 \ \text{Area}}{\text{Standard} \ T_3 \ \text{Area}} \times \dfrac{\text{Std} \ T_3 \ \text{conc.} \ (\mu g)}{(ml)} \times 50 \ ml = \mu g \ T_3$$

The specification is NGT 2.0% liothyronine calculated as follows:

$$\text{Amt} \ T_3 \ \text{Assayed} \ (\mu g) \times 100 = \dfrac{\% \ \text{LIOTHYRONINE}}{\text{Amt} \ T_4 \ \text{Assayed} \ (\mu g)^*}$$

*This number is calculated using the $T_4$ potency results as follows:

$$\dfrac{\text{Sample} \ T_4 \ \text{Area}}{\text{Standard} \ T_4 \ \text{Area}} \times \dfrac{\text{Std} \ T_4 \ \text{conc.} \ (\mu g)}{(ml)} \times 50 \ ml \times \dfrac{798.86}{776.87} = \mu g \ T_4$$

where  798.86 = molecular weight of Levothyroxine as the Sodium Salt
       776.87 = molecular weight of Levothyroxine Standard Base

TABLE 11-continued

QC - 001 T3 Test Procedure

| | |
|---|---|
| NOTE: | If the single active ingredient comprises 50% or more, by weight, of the dosage unit, use Method A; otherwise use Method B. |
| METHOD: | USP 24 <905> pp. 2000–2002. |
| METHOD A: | Content Uniformity as Determined by Weight Variation:<br>Weight accurately 10 tablets, individually. From the results of the average potency of the active ingredient determined for the product (using the assay methods as stated in the individual monograph) calculate the content of active ingredient in each of the 10 tablets. |
| CALCULATIONS: | $\text{Individual Potency} = \dfrac{(\text{Avg. potency})(\text{Individual Wt.})}{\text{Avg. tablet weight}}$ |
| NOTE: | If the active ingredient(s) are less than 50% by weight of the tablet content, refer to the individual test method for potency for those products. |
| METHOD B: | Content Uniformity as Determined by Direct Assay of Active Ingredient: For Levothyroxine Sodium tablets the following procedure is followed. Individually weigh 10 tablets. Place the 10 individual tablets into round bottomed test tubes or flasks of the appropriate size as outlined in the chart below. Add the appropriate volume of extraction mobile comprised of water, acetonitrile, and phosphoric acid (65:35::0.05) to each test tube or flask as indicated in the chart below. Note: All test tubes are to be capped with screw on caps and all flasks are to be covered with parafilm as soon as mobile phase is added. Allow to stand at room temperature until the tablet completely crumbles. Secure all samples in a wrist action shaker. Test tubes are to be secured horizontally. Erlenmeyer flasks are to be secured vertically. Set the wrist shaker to the setting specified in the table. Shake sample for 3 minutes. Transfer about 10 ml of the sample preparation (or the entirety of smaller samples) to a centrifuge tube. Centrifuge samples for 1 minute at about 3000 rpm. Transfer samples to autosampler vials using disposable Pasteur pipettes. Utilize the HPLC Method for levothyroxine separation (AM-003) for obtaining dosage uniformity, sample area, and standard area results. |
| CALCULATIONS: | Dosage Uniformity Result (% Label Claim)<br>$\dfrac{798.86}{776.87} \times \dfrac{\text{Area of Sample}}{\text{Area of Std.}} \times \dfrac{\text{Conc. of Std.}}{\text{Conc. Of Sample}} \times 100 = \% \text{ Potency}$<br>(See chart below) |

SPECIFICATIONS FOR METHOD A OR METHOD B

| | |
|---|---|
| S-1 | The % active ingredient for 10 tablets tested must fall in the range of 85.0%–115.0% and the RSD of the 10 tablets must not exceed 6.0%. |
| NOTE: | If 1 unit in S-1 fails to meet either of the specifications, but is no outside the range of 75%–125%, test 20 more units and proceed to S-2. |
| S-2 | When n = 30, NGT one unit outside 85.0–115.0%, none outside 75.0–125.0% and RSD NGT 7.80%. |

Results:

Results for a variety of dosages, using a sample size of 120 pills, are shown in Table 12.

TABLE 12

Dosage Consistency - 120 pill samples

| Dosage | 25 μg | 100 μg | 300 μg |
|---|---|---|---|
| Label Claim Activity | 103.5% | 103.1% | 102.9% |
| High | 109.1% | 104.8% | 108.8% |
| Low | 98.0% | 100.7% | 96.5% |
| RSD | <2.0% | 0.9% | 2.2% |

The results confirm an extremely low amount of variability in active material content between the 120 pills tested. Generally the variability for a 120 pill sample should be between about 90 and about 110% of claimed activity, preferably between about 95% and about 105%. The RSD for a 120 pill sample should not be greater than 5%, and preferably is less than 3%.

EXAMPLE 7

Levothyroxine Sodium Release Specification and Analytical Methods

The specifications for levothyroxine sodium tablets are stated in: USP 24 page 969–970 and Supplement 1 page 2638. The additional requirements are in place to ensure the tablet appearance, for the individual tablet strengths, is correct and the physical characteristics ensure a quality tablet.

A. Analytical Methods

All the test methods utilized in the testing of levothyroxine sodium meet USP system suitability requirements. All Levoxyl® batches are tested for conformance to the following specifications. The Table 13 below lists the test parameter, specification and the test method employed.

TABLE 13

| Test Parameter | Specification | Test Method |
|---|---|---|
| USP Specifications | | |
| Tablet Potency | 90.0–110.0% label claim* | AM-003 |
| Tablet Dissolution | NULT 7580% label claim dissoluted in 145 minutes | AM-004B |
| Liothyronine Content | NGT 2.0% | QC-001 |
| TLC Identification | Compares to Standard | RM-054 |
| Uniformity of Dosage Units | S-1: 85.0–115.0% RSD NGT 6.0% n = 10 (if NGT 1 unit fails, but no unit is outside range of 75.0–125.0% or if RSD fails proceed to S-2) S-2: When n = 30 NGT 1 unit outside 85.0–115.0%, none outside 75.0–125.0% and RSD NGT 7.8% | QC-003 |
| Additional Requirements: | | |
| Tablet Hardness | 6.0–14.0 KP | QC-005 |
| Tablet Weight | 142.0–149.0 mg | QC-007 |
| Tablet Appearance | Color, imprint, score and shape conform to specific tablet parameters as specified for the individual strengths | QC-008 |

EXAMPLE 8

Bioavailability Determination of Two Levothyroxine Formulations

The following example was performed along lines of a 1999 FDA publication entitled *In-Vivo Pharmacokinetics and Bioavailability Studies and In-Vitro Dissolution Testing for Levothyroxine Sodium Tablets*. The example includes the following two studies.

Study 1. Single-Dose Bioavailability Study:

The objective of the study was to determine the bioavailability of Levoxyl® relative to a reference (oral solution) under fasting conditions.

Study 2: Dosage-Form Equivalence Study:

The objective of the study was to determine the dosage-form bioequivalence between three different strengths of Levoxyl® tablets (low, middle and high range).

Study Objective:

To determine the bioavailability of levothyroxine sodium (Levoxyl®) 0.3 mg tablets manufactured by JONES PHARMA INCORPORATED, relative to Knoll Pharmaceutical Company's levothyroxine sodium 200 µg (Synthroid®) injection given as an oral solution following a single 0.6 mg dose.

Study Methodology:

Single-dose, randomized, open-label, two-way crossover design.

Protocol Reference:

Guidance for Industry: In Vivo Pharmacokinetics and Bioavailability Studies and In Vitro Dissolution Testing for Levothyroxine Sodium Tablets (June 1999).

Number of Subjects:

A total of 30 subjects were enrolled in the study, and 27 subjects completed the study. All 30 subjects were included in the safety analysis and 27 subjects who completed the study were included in the pharmacokinetic analyses.

Diagnosis and Main Criteria for Inclusion:

All subjects enrolled in this study were judged by the investigator to be healthy volunteers who met all inclusion and exclusion criteria.

Test Product, Dose, Duration, Mode of Administration, and Batch Number:

The test product was levothyroxine sodium (Levoxyl®) 2×0.3 mg tablets administered as a single oral dose. The batch number utilized in this study was TT26.

Reference Product, Dose, Duration, Mode of Administration, and Batch Number:

The reference product was levothyroxine sodium (Synthroid®) 2×500 µg injection vials (Knoll Pharmaceutical Company) reconstituted and 600 µg administered orally. The reference product used was the 500 µg injection instead of 200 µg due to the unavailability of sufficient quantities of 200 µg injection to conduct the study. The batch number utilized in this study was 80130028.

Criteria for Evaluation:

Pharmacokinetics:

Pharmacokinetic assessment consisted of the determination of total (bound+free) T4 and T3 concentrations in serum at specified time points following drug administration. From the serum data, the parameters AUC(0-t), Cmax, and Tmax were calculated.

Safety:

Safety assessment included vital signs, clinical laboratory evaluation (including TSH), physical examination, and adverse events (AEs) assessment.

Statistical Methods

Pharmacokinetics:

Descriptive statistics (arithmetic mean, standard deviation (SD), coefficient of variation (CV), standard error of the mean (SE), sample size (N), minimum, and maximum) were provided for all pharmacokinetic parameters. The effects of baseline and baseline-by treatment interaction were evaluated using a parametric (normal-theory) general linear model (ANCOVA) with treatment, period, sequence, subject within sequence, ln(baseline), and interaction between ln(baseline) and treatment as factors, applied to the ln-transformed pharmacokinetic parameters and Cmax. In the absence of significant ln(baseline) and interaction between ln(baseline)and treatment, these parameters were removed from the model. The two one-sided hypotheses were tested at the 5% level of significance for ln[AUC(0-t)] and ln(Cmax) by constructing 90% confidence intervals for the ratio of Treatment A to Treatment Safety:

Frequency counts of all subjects enrolled in the study, completing the study, and discontinuing early were tabulated. Descriptive statistics were calculated for continuous demographic variables, and frequency counts were tabulated for categorical demographic variables for each gender and overall.

AEs were coded using the $5^{th}$ Edition of the COSTART dictionary. AEs were summarized by the number and percentage of subjects experiencing each coded event. A summary of the total number of each coded event and as a percentage of total AEs was also provided.

Laboratory summary tables included descriptive statistics for continuous serum chemistry and hematology results at each time point. Out-of-range values were listed by subject for each laboratory parameter.

Descriptive statistics for vital sign measurements at each time point and change from baseline to each time point were calculated by treatment group. Shifts from screening to post study results for physical examinations were tabulated.

Pharmacokinetic Results—T4:

ANCOVA analyses indicated that the effects of ln(baseline) and interaction between ln(baseline) and treatment were not significant. Thus, these factors were removed from the general linear model and an ANOVA with treatment, period, sequence, and subject within sequence was applied to the ln-transformed Cmax and AUC(0-t) parameters. The arithmetic means of serum T4 pharmacokinetic parameters for Treatments A and B and the statistical comparison for ln-transformed parameters are summarized in the following table.

Summary of the Pharmacokinetic Parameters of Serum T4 for Treatments A and B

| Pharmacokinetic Parameters | Treatment A* | | Treatment B** | | 90% CI | % Mean Ratio |
|---|---|---|---|---|---|---|
| | Arithmetic Mean | SD | Arithmetic Mean | SD | | |
| Cmax (uμg/dIL) | 14.48 | 1.93 | 15.09 | 2.10 | — | — |
| Tmax (hr) | 2.17 | 0.810 | 1.62 | 0.502 | — | — |
| AUC (0-t) (μg*hr/dl) | 524.3 | 59.07 | 529.3 | 62.83 | — | — |
| ln (Cmax) | 2.663 | 0.1434 | 2.705 | 0.1339 | 91.1–98.1 | 94.5 |
| ln [AUC (0-t)] | 6.256 | 0.1167 | 6.265 | 0.1169 | 95.6–100.5 | 98.0 |

*Treatment A = 2 × 0.3 mg Levoxyl ® Tablets: test
**Treatment B = 0.6 mg Synthroid Reconstitute Oral Solution: reference Pharmacokinetics Results—T3:

ANCOVA analyses indicated that the effects of ln(baseline) and interaction between ln(baseline) and treatment were not significant and were removed from the ANOVA model, except for ln(baseline) on ln(Cmax) which was significant and was kept in the model. An ANOVA with treatment, period, sequence, and subject within sequence, and ln(baseline), when significant, was applied to the ln-transformed Cmax and AUC(0-t) parameters. The arithmetic means of serum T3 pharmacokinetic parameters for Treatments A and B and the statistical comparison for ln-transformed parameters are summarized in the following table.

Summary of the Pharmacokinetic Parameters of Serum T3 for Treatments A and B

| Pharmacokinetic Parameters | Treatment A* | | Treatment B** | | 90% CI | % Mean Ratio |
|---|---|---|---|---|---|---|
| | Arithmetic Mean | SD | Arithmetic Mean | SD | | |
| Cmax (ng/ml) | 1.165 | 0.156 | 1.140 | 0.119 | — | — |
| Tmax (hr) | 14.6 | 15.2 | 16.3 | 17.0 | — | — |
| AUC (0-t) (ng*hr/ml) | 51.25 | 6.163 | 50.07 | 5.311 | — | — |
| ln (Cmax) | 0.1444 | 0.1289 | 0.1255 | 0.1034 | 96.8–103.4 | 100.0 |
| ln [AUC (0-t)] | 3.930 | 0.1209 | 3.908 | 0.1059 | 97.7–103.8 | 100.7 |

*Treatment A = 2 × 0.3 mg Levoxyl ® Tablets: test
**Treatment B = 0.6 mg Synthroid Reconstitute Oral Solution: reference Comparison of total T4 and T3 pharmacokinetics following administration of Levoxyl® (Treatment A, test formulation) and Synthroid (Treatment B, reference formulation) indicated that the test formulation met the requirements for bioequivalence with the reference formulation.

The 90% confidence intervals for the comparisons of ln(Cmax) and ln[AUC(0-t)] for T4 and T3 were within the 80% to 125% range required for bioequivalence.

In regard to subject safety, both treatments appeared to be equally safe and well tolerated.

EXAMPLE 9

Bioavailability Study to Assess Single Dose Bioequivalence of Three Strengths of Levothyroxine The following example was performed to determine the dosage-form bioequivalence between three different strengths of levothyroxine sodium (Levoxyl®) tablets following a single 600 mcg dose.
Study Methodology:
Single-dose, randomized, open-label, three-way crossover design.
Protocol Reference:
Guidance for Industry: In Vivo Pharmacokinetics and Bioavailability Studies and In Vitro Dissolution Testing for Levothyroxine Sodium Tablets (June 1999). This protocol was submitted in IND 59,177.

Number of Subjects:

A total of 28 subjects were enrolled in the study, and 24 subjects completed the study. All 28 subjects were included in the safety analysis and 24 subjects who completed the study were included in the pharmacokinetic analyses.

Diagnosis and Main Criteria for Inclusion:

All subjects enrolled in this study were judged by the investigator to be healthy volunteers who met all inclusion and exclusion criteria.

Test Product, Dose, Duration, Mode of Administration, and Batch Number:

Subjects randomized to Treatment A received a single oral dose of 12×50 mcg levothyroxine sodium (Levoxyl®) tablets, Lot No. TT24. Subjects randomized to Treatment B received 6×100 mcg levothyroxine sodium (Levoxyl®) tablets, Lot No.TT25. Subjects randomized to Treatment C received 2×300 mcg levothyroxine sodium (Levoxyl®) tablets, Lot No. TT26. Test products were manufactured by JMI-Daniels, a subsidiary of Jones Pharma Incorporated.

Pharmacokinetics:

Pharmacokinetic assessment consisted of the determination of total (bound+free) T4 and T3 concentrations in serum at specified time points following drug administration. From the serum data, the parameters AUC(0-t), Cmax, and Tmax were calculated.

Safety:

Safety assessment included monitoring of sitting vital signs, clinical laboratory measurements, thyroid-stimulating hormone (TSH), physical examination, electrocardiogram (ECG), and adverse events (AEs).

Statistical Methods

Pharmacokinetics:

Descriptive statistics (arithmetic mean, standard deviation (SD), coefficient of variation (CV), standard error of the mean (SEM), sample size (N), minimum, and maximum) were provided for all pharmacokinetic parameters. A parametric (normal-theory) general linear model with treatment, period, sequence, and subject within sequence as factors was applied to the ln-transformed Cmax and AUC(0-t). The two one-sided hypotheses were tested at the 5% level of significance for ln[AUC(0-t)] and In(Cmax) by constructing 90% confidence intervals for the ratios of Treatment A to Treatment B, Treatment A to Treatment C, and Treatment B to Treatment C.

Safety:

Frequency counts of all subjects enrolled in the study, completing the study, and discontinuing early were tabulated. Descriptive statistics were calculated for continuous demographic variables, and frequency counts were tabulated for categorical demographic variables for each gender and overall.

AEs were coded using the $5^{th}$ Edition of the COSTART dictionary. AEs were summarized by the number and percentage of subjects experiencing each coded event. A summary of the total number of each coded event and as a percentage of total AEs was also provided. Laboratory summary tables included descriptive statistics for continuous serum chemistry and hematology results at each time point. Out-of-range values were listed by subject for each laboratory parameter. Descriptive statistics for vital sign measurements at each time point and change from baseline to each time point were calculated by treatment group. Shifts from screening to post study results for physical examinations were tabulated.

Pharmacokinetic Resulta—T4:

The arithmetic means of serum T4 pharmacokinetic parameters for Treatments A and B and the statistical comparison for the ln-transformed parameters are summarized in the following table.

Summary of the Pharmacokinetic Parameters of Serum T4 for Treatments A and B

| Pharmacokinetic Parameters | Treatment A* | | Treatment B** | | 90% CI | % Mean Ratio |
|---|---|---|---|---|---|---|
| | Arithmetic Mean | SD | Arithmetic Mean | SD | | |
| Cmax (µg/dl) | 13.70 | 1.82 | 14.13 | 1.48 | — | — |
| Tmax (hr) | 2.37 | 1.04 | 1.98 | 0.827 | — | — |
| AUC (0-t) (µg*hr/dl) | 509.0 | 58.36 | 528.3 | 72.41 | — | — |
| ln (Cmax) | 2.609 | 0.1378 | 2.643 | 0.1095 | 93.6–100.1 | 96.8 |
| ln [AUC (0-t)] | 6.226 | 0.1200 | 6.261 | 0.1379 | 93.4–100.0 | 96.7 |

*Treatment A = 12 × 50 mcg Levoxyl ® Tablets
**Treatment B = 6 × 100 mcg Levoxyl ® Tablets The arithmetic means of serum T4 pharmacokinetic parameters for Treatments A and C and the statistical comparison for the ln-transformed parameters are summarized in the following table.

Summary of the Pharmacokinetic Parameters of Serum T4 for Treatments A and C

| Pharmacokinetic Parameters | Treatment A* | | Treatment C** | | 90% CI | % Mean Ratio |
|---|---|---|---|---|---|---|
| | Arithmetic Mean | SD | Arithmetic Mean | SD | | |
| Cmax (µg/dl) | 13.70 | 1.82 | 14.15 | 1.50 | — | — |
| Tmax (hr) | 2.37 | 1.04 | 2.40 | 1.09 | — | — |
| AUC (0-t) (µg*hr/dL1) | 509.0 | 58.36 | 528.7 | 57.13 | — | — |

-continued

|  | Treatment A* | | Treatment C** | | | |
|---|---|---|---|---|---|---|
| Pharmacokinetic Parameters | Arithmetic Mean | SD | Arithmetic Mean | SD | 90% CI | % Mean Ratio |
| ln (Cmax) | 2.609 | 0.1378 | 2.644 | 0.1085 | 93.6–100.1 | 96.8 |
| ln [AUC (0-t)] | 6.226 | 0.1200 | 6.265 | 0.1089 | 93.1–99.7 | 96.4 |

*Treatment A = 12 × 50 mcg Levoxyl ® Tablets
**Treatment C = 2 × 300 mcg Levoxyl ® Tablets The arithmetic means of serum T4 pharmacokinetic parameters for Treatments B and C and the statistical comparison for the ln-transformed parameters are summarized in the following table.

Pharmacokinetic Results—T4 (Continued):

Summary of the Pharmacokinetic Parameters of Serum T4 for Treatments B and C

|  | Treatment B* | | Treatment C** | | | |
|---|---|---|---|---|---|---|
| Pharmacokinetic Parameters | Arithmetic Mean | SD | Arithmetic Mean | SD | 90% CI | % Mean Ratio |
| Cmax (μg/dl) | 14.13 | 1.48 | 14.15 | 1.50 | — | — |
| Tmax (hr) | 1.98 | 0.827 | 2.40 | 1.09 | — | — |
| AUC (0-t) (μg*hr/dl) | 528.3 | 72.41 | 528.7 | 57.13 | | |
| ln (Cmax) | 2.643 | 0.1095 | 2.644 | 0.1085 | 96.7–103.4 | 100.0 |
| ln [AUC (0-t)] | 6.261 | 0.1379 | 6.265 | 0.1089 | 96.4–103.1 | 99.7 |

*Treatment B = 6 × 100 mcg Levoxyl ® Tablets
**Treatment C = 2 × 300 mcg Levoxyl ® Tablets Pharmacokinetic Results—T3:

The arithmetic means of serum T3 pharmacokinetic parameters for Treatments A and B and the statistical comparison for the ln-transformed parameters are summarized in the following table.

Summary of the Pharmacokinetic Parameters of Serum T3 for Treatments A and B

|  | Treatment A* | | Treatment B** | | | |
|---|---|---|---|---|---|---|
| Pharmacokinetic Parameters | Arithmetic Mean | SD | Arithmetic Mean | SD | 90% CI | % Mean Ratio |
| Cmax (ng/ml) | 1.173 | 0.138 | 1.142 | 0.133 | — | — |
| Tmax (hr) | 12.9 | 19.0 | 12.1 | 16.1 | — | — |
| AUC (0-t) (ng*hr/ml) | 49.43 | 6.872 | 50.35 | 8.994 | — | — |
| ln (Cmax) | 0.1523 | 0.1226 | 0.1264 | 0.1194 | 98.1–107.3 | 102.6 |
| ln [AUC (0-t)] | 3.890 | 0.1538 | 3.905 | 0.1731 | 93.1–104.3 | 98.5 |

*Treatment A = 12 × 50 mcg Levoxyl ® Tablets
**Treatment B = 6 × 100 mcg Levoxyl ® Tablets The arithmetic means of serum T3 pharmacokinetic parameters for Treatments A and C and the statistical comparison for the ln-transformed parameters are summarized in the following table.

Pharmnacokinetic Results—T3 (Continued):

Summary of the Pharmacokinetic Parameters of Serum T3 for Treatments A and C

| Pharmacokinetic Parameters | Treatment A* | | Treatment C** | | 90% CI | % Mean Ratio |
|---|---|---|---|---|---|---|
| | Arithmetic Mean | SD | Arithmetic Mean | SD | | |
| Cmax (ng/ml) | 1.173 | 0.138 | 1.167 | 0.169 | — | — |
| Tmax (hr) | 12.9 | 19.0 | 11.5 | 16.4 | — | — |
| AUC (0-t) (ng*hr/ml) | 49.43 | 6.872 | 49.36 | 7.680 | — | — |
| ln (Cmax) | 0.1523 | 0.1226 | 0.1437 | 0.1491 | 96.3–105.4 | 100.7 |
| ln [AUC (0-t)] | 3.890 | 0.1538 | 3.886 | 0.1705 | 94.7–106.2 | 100.3 |

*Treatment A = 12 × 50 mcg Levoxyl ® Tablets
**Treatment C = 2 × 300 mcg Levoxyl ® Tablets The arithmetic means of serum T3 pharmacokinetic parameters for Treatments B and C and the statistical comparison for the ln-transformed parameters are summarized in the following table.

Summary of the Pharmacokinetic Parameters of Serum T3 for Treatments B and C

| Pharmacokinetic Parameters | Treatment B* | | Treatment C** | | 90% CI | % Mean Ratio |
|---|---|---|---|---|---|---|
| | Arithmetic Mean | SD | Arithmetic Mean | SD | | |
| Cmax (ng/ml) | 1.142 | 0.133 | 1.167 | 0.169 | — | — |
| Tmax (hr) | 12.1 | 16.1 | 11.5 | 16.4 | — | — |
| AUC (0-t) (ng*hr/ml) | 50.35 | 8.994 | 49.36 | 7.680 | — | — |
| ln (Cmax) | 0.1264 | 0.1194 | 0.1437 | 0.1491 | 93.9–102.7 | 98.2 |
| ln [AUC (0-t)] | 3.905 | 0.1731 | 3.886 | 0.1705 | 96.2–107.8 | 101.8 |

*Treatment B = 6 × 100 mcg Levoxyl ® Tablets
**Treatment C = 2 × 300 mcg Levoxyl ® Tablets Safety Results:

There was a total of 59 treatment-emergent AEs reported by 15 (54%) of the 28 subjects dosed with study treatment. Incidence of AEs was similar across treatments. Headache was the most frequently reported event. The majority of the AEs were mild in intensity. There was one subject who experienced a serious adverse event of chest pain, considered by the Investigator to be unrelated to treatment. No trends were noted in vital signs, clinical laboratory results, or ECGs to suggest treatment-related differences.

Comparison of total T4 and T3 pharmacokinetics following administration of 12×50 mcg Levoxyl® tablets (Treatment A) and 6×100 mcg Levoxyl® tablets (Treatment B) indicated that the two formulations met the requirements for bioequivalence. The 90% confidence intervals for the comparisons of ln(Cmax) and ln[AUC(0-t)] for T4 and T3 were within the 80% to 125% range required for bioequivalence.

Comparison of total T4 and T3 pharmacokinetics following administration of 12×50 mcg Levoxyl® tablets (Treatment A) and 2×300 mcg Levoxyl® tablets (Treatment C) indicated that the two formulations met the requirements for bioequivalence. The 90% confidence intervals for the comparisons of ln(Cmax) and ln[AUC(0-t)] for T4 and T3 were within the 80% to 125% range required for bioequivalence.

Comparison of total T4 and T3 pharmacokinetics following administration of 6×100 mcg Levoxyl® tablets (Treatment B) and 2×300 mcg Levoxyl® tablets (Treatment C) indicated that the two formulations met the requirements for bioequivalence. The 90% confidence intervals for the comparisons of ln(Cmax) and ln[AUC(0-t)] for T4 and T3 were within the 80% to 125% range required for bioequivalence.

The test formnulations appear to be safe and generally well tolerated when given to healthy adult volunteers.

EXAMPLE 10

Levothyroxine Sodium (Levoxyl®) Tablet Compositions

The following preferred levothroxine sodium compositions in tablet form were made along lines disclosed herein.

Levoxyl® 25 meg Tablets

Color: orange; Markings: (front) dp/25 (back) LEVOXYL®

| Component | Quantity in mg/Tablet |
|---|---|
| Levothyroxine Sodium, USP | 0.025 mg |
| β-Form Microcrystalline Cellulose, NF (Ceolus ®) | 108.529 mg |
| Croscarmellose Sodium, NF (Ac-di-sol ®) | 35.079 mg |
| FD&C Yellow #6 | 0.352 mg |
| Magnesium Stearate, NF | 1.018 mg |

Levoxyl® 50 mcg Tablets

Color: white; Markings: (front) dp/50 (back) LEVOXYL®

| Component | Quantity in mg/Tablet |
| --- | --- |
| Levothyroxine Sodium, USP | 0.050 mg |
| β-Form Microcrystalline Cellulose, NF (Ceolus ®) | 108.856 mg |
| Croscarmellose Sodium, NF (Ac-di-sol ®) | 35.079 mg |
| Magnesium Stearate, NF | 1.018 mg |

Levoxyl® 75 mcg Tablets

Color: purple; Markings: (front) dp/75 (back) LEVOXYL®

| Component | Quantity in mg/Tablet |
| --- | --- |
| Levothyroxine Sodium, USP | 0.075 mg |
| β-Form Microcrystalline Cellulose, NF (Ceolus ®) | 108.438 mg |
| Croscarmellose Sodium, NF (Ac-di-sol ®) | 35.079 mg |
| Lake Blend #LB-1609 (Blend of D&C Red #30 and FD&C Blue #1) | 0.383 mg |
| Magnesium Stearate, NF | 1.018 mg |

Levoxyl® 88 mcg Tablets

Color: olive; Markings: (front) dp/88 (back) LEVOXYL®

| Component | Quantity in mg/Tablet |
| --- | --- |
| Levothyroxine Sodium, USP | 0.088 mg |
| β-Form Microcrystalline Cellulose, NF (Ceolus ®) | 108.311 mg |
| Croscarmellose Sodium, NF (Ac-di-sol ®) | 35.079 mg |
| Lake Blend #LB-1607 (Blend of FD&C Yellow #6, D&C Red #30 and FD&C Blue #1) | 0.507 mg |
| Magnesium Stearate, NF | 1.018 mg |

Levoxyl® 100 mcg Tablets

Color: yellow; Markings: (front) dp/100 (back) LEVOXYL®

| Component | Quantity in mg/Tablet |
| --- | --- |
| Levothyroxine Sodium, USP | 0.100 mg |
| β-Form Microcrystalline Cellulose, NF (Ceolus ®) | 108.406 mg |
| Croscarmellose Sodium, NF (Ac-di-sol ®) | 35.079 mg |
| Lake Blend #LB-282 (Blend of FD&C Yellow #6 and D&C Yellow #10) | 0.388 mg |
| Magnesium Stearate, NF | 1.018 mg |

Levoxyl® 112 mcg Tablets

Color: rose; Markings: (front) dp/112 (back) LEVOXYL®

| Component | Quantity in mg/Tablet |
| --- | --- |
| Levothyroxine Sodium, USP | 0.112 mg |
| β-Form Microcrystalline Cellulose, NF (Ceolus ®) | 107.711 mg |
| Croscarmellose Sodium, NF (Ac-di-sol ®) | 35.079 mg |
| Lake Blend #LB-1610 (Blend of FD&C Yellow #6, D&C Red #30 and FD&C Red #40) | 1.080 mg |
| Magnesium Stearate, NF | 1.018 mg |

Levoxyl® 125 mcg Tablets

Color: brown; Markings: (front) dp/125 (back) LEVOXYL®

| Component | Quantity in mg/Tablet |
| --- | --- |
| Levothyroxine Sodium, USP | 0.125 mg |
| β-Form Microcrystalline Cellulose, NF (Ceolus ®) | 108.701 mg |
| Croscarmellose Sodium, NF (Ac-di-sol ®) | 35.079 mg |
| Lake Blend # LB-1617 (Blend of D&C Yellow # 10 and FD&C Red # 40) | 0.080 mg |
| Magnesium Stearate, NF | 1.018 mg |

Levoxyl® 137 mcg Tablets

Color: dark blue; Markings: (front) dp/137 (back) LEVOXYL®

| Component | Quantity in mg/Tablet |
| --- | --- |
| Levothyroxine Sodium, USP | 0.137 mg |
| β-Form Microcrystalline Cellulose, NF (Ceolus ®) | 108.288 mg |
| Croscarmellose Sodium, NF (Ac-di-sol ®) | 35.079 mg |
| FD&C Blue # 1 | 0.478 mg |
| Magnesium Stearate, NF | 1.018 mg |

Levoxyl® 150 mcg Tablets

Color: blue; Markings: (front) dp/150 (back) LEVOXYL®

| Component | Quantity in mg/Tablet |
| --- | --- |
| Levothyroxine Sodium, USP | 0.150 mg |
| β-Form Microcrystalline Cellulose, NF (Ceolus ®) | 108.645 mg |
| Croscarmellose Sodium, NF (Ac-di-sol ®) | 35.079 mg |
| Lake Blend # LB-1612 (Blend of D&C Red # 30 and FD&C Blue # 1) | 0.108 mg |
| Magnesium Stearate, NF | 1.018 mg |

Levoxyl® 175 mcg Tablets

Color: turquoise; Markings: (front) dp/175 (back) LEVOXYL®

| Component | Quantity in mg/Tablet |
|---|---|
| Levothyroxine Sodium, USP | 0.175 mg |
| β-Form Microcrystalline Cellulose, NF (Ceolus ®) | 108.397 mg |
| Croscarmellose Sodium, NF (Ac-di-sol ®) | 35.079 mg |
| Lake Blend # LB-334 (Blend of D&C Yellow # 10, and FD&C Blue # 1) | 0.334 mg |
| Magnesium Stearate, NF | 1.018 mg |

Levoxyl® 200 mcg Tablets

Color: pink; Markings: (front) dp/200 (back) LEVOXYL®

| Component | Quantity in mg/Tablet |
|---|---|
| Levothyroxine Sodium, USP | 0.200 mg |
| β-Form Microcrystalline Cellulose, NF (Ceolus ®) | 108.515 mg |
| Croscarmellose Sodium, NF (Ac-di-sol ®) | 35.079 mg |
| Lake Blend # LB-1613 (Blend of D&C Yellow # 10 and D&C Red # 30) | 0.188 mg |
| Magnesium Stearate, NF | 1.018 mg |

Levoxyl® 300 mcg Tablets

Color: green; Markings: (front) dp/300 (back) LEVOXYL®

| Component | Quantity in mg/Tablet |
|---|---|
| Levothyroxine Sodium, USP | 0.300 mg |
| β-Form Microcrystalline Cellulose, NF (Ceolus ®) | 108.451 mg |
| Croscarmellose Sodium, NF (Ac-di-sol ®) | 35.079 mg |
| Lake Blend # LB-1614 (Blend of FD&C Yellow # 6, D&C Yellow # 10 and FD&C Blue # 1) | 0.142 mg |
| Magnesium Stearate, NF | 1.018 mg |

While the present invention has been described in the context of preferred embodiments and examples, it will be readily apparent to those skilled in the art that other modifications and variations can be made therein without departing from the spirit or scope of the present invention. For example, the active moiety levothyroxine sodium can be changed to liothyronine sodium and similar products and still be considered as part of the claimed invention. Accordingly, it is not intended that the present invention be limited to the specifics of the foregoing description of the preferred embodiments and examples, but rather as being limited only by the scope of the invention as defined in the claims appended hereto.

Having described our invention, we claim:

1. A stable, solid, immediate release pharmaceutical composition for oral administration to treat a thyroid disorder, said composition comprising:

(a) about 0.00005 wt % to about 5 wt % of a levothyroxine salt;

(b) at least about 50 wt % of a β-form microcrystalline cellulose particles, said β-form microcrystalline cellulose particles having generally flat needle-shapes, a bulk density in a range of from about 0.10 g/cm³ to about 0.23 g/cm³, and a conductivity of less than about 200 µS/cm; and (c) about 0.5 wt % to about 30 wt % disintegrating agent; wherein (1) at least about 90 wt % of the levothyroxine salt in the composition dissolves in an aqueous solution in less than about 5 minutes, (2) potency loss for said levothyroxine salt is no more than about 0.3% per month for a period of at least about 18 months, and (3) said composition is essentially sugar-free.

2. A stable, solid, immediate release pharmaceutical composition of claim 1, wherein at least about 90 wt % of the levothyroxine salt in the composition dissolves in an aqueous solution in less than about 2.5 minutes.

3. A stable, solid, immediate release pharmaceutical composition of claim 1, wherein said pharmaceutical composition exhibits a levothyroxine (T4) plasma Cmax of from between about 10 µg/dL to about 20 µg/dL.

4. A stable, solid, immediate release pharmaceutical composition of claim 1, wherein said pharmaceutical composition exhibits a levothyroxine (T4) plasma Cmax of from between about 12 µg/dL to about 16 µg/dL.

5. A stable, solid, immediate release pharmaceutical composition of claim 1, wherein said pharmaceutical composition exhibits a triiodothyronine (T3) plasma Cmax of from between about 0.1 ng/mL to about 10 ng/mL.

6. A stable, solid, immediate release pharmaceutical composition of claim 1, wherein said pharmaceutical composition exhibits a triiodothyronine (T3) plasma Cmax of from between about 0.5 ng/mL to about 2 ng/mL.

7. A stable, solid, immediate release pharmaceutical composition of claim 1, wherein said pharmaceutical composition exhibits a levothyroxine (T4) plasma Tmax of from between about 1 hours to about 3 hours.

8. A stable, solid, immediate release pharmaceutical composition of claim 1, wherein said pharmaceutical composition exhibits a triiodothyronine (T3) plasma Tmax of from between about 12 hours to about 16 hours.

9. A stable, solid, immediate release pharmaceutical composition of claim 1, wherein said pharmaceutical composition exhibits a levothyroxine (T4) AUC(0-t) of between from about 500 µg-hour/dL to about 550 µg-hour/dL.

10. A stable, solid, immediate release pharmaceutical composition of claim 1, wherein said pharmaceutical composition exhibits a triiodothyronine (T3) AUC(0-t) of between from about 20 ng-hour/mL to about 60 ng-hour/mL.

11. A stable, solid, immediate release pharmaceutical composition of claim 1, wherein said pharmaceutical composition is a non-granular composition.

12. A stable, solid, immediate release pharmaceutical composition of claim 1, wherein said β-form microcrystalline cellulose particles have a bulk density in a range of from about 0.17 g/cm³ to about 0.23 g/cm³.

13. A stable, solid, immediate release pharmaceutical composition of claim 1, wherein said pharmaceutical composition is formulated as a tablet.

14. A stable, solid, immediate release pharmaceutical composition of claim 13, wherein said tablet has a total hardness of from between about 5 KP to about 15 KP.

15. A stable, solid, immediate release pharmaceutical composition of claim 13, wherein said tablet has a surface area of from between about 0.9 in.² to about 15 in.².

16. A stable, solid, immediate release pharmaceutical composition of claim 13, wherein said tablet is beveled.

17. A stable, solid, immediate release pharmaceutical composition of claim 13, wherein said tablet is scored.

18. A stable, solid, immediate release pharmaceutical composition of claim 13, wherein said tablet has a raised violin configuration.

19. A stable, solid, immediate release pharmaceutical composition of claim 1, wherein said pharmaceutical composition includes less than about 10% total impurities.

20. A stable, solid, immediate release pharmaceutical composition of claim 1, wherein said pharmaceutical composition includes less than about 5% total impurities.

21. A stable, solid, immediate release pharmaceutical composition of claim 1, wherein said disintegrant is a croscarmellose salt.

22. A stable, solid, immediate release pharmaceutical composition of claim 1, wherein said pharmaceutical composition further includes at least one pharmaceutically acceptable coloring agent.

23. A stable, solid, immediate release pharmaceutical tablet for oral consumption comprising:
   (a) between from about 0.01 mg to about 0.8 mg levothyroxine sodium;
   (b) between from about 100 mg to about 110 mg of β-microcrystalline cellulose particles, said β-form microcrystalline cellulose particles having generally flat needle-shapes, a bulk density in a range of from about 0.10 g/cm$^3$ to about 0.23 g/cm$^3$, and a conductivity of less than about 200 μS/cm;
   (c) between from about 25 mg to about 50 mg of croscarmellose sodium; and
   (d) between from about 0.5 mg to about 5 mg of magnesium stearate,
wherein (1) at least about 90 wt % of the levothyroxine salt in the composition dissolves in an aqueous solution in less than about 5 minutes, (2) potency loss for said levothyroxine salt is no more than about 0.3% per month for a period of at least about 18 months, and (3) said composition is essentially sugar-free.

24. A stable, solid, immediate release pharmaceutical tablet of claim 23, wherein said tablet further includes at least one pharmaceutically acceptable coloring agent.

25. A stable, solid, immediate release pharmaceutical composition for oral administration to treat a thyroid disorder, said composition comprising:
   (a) about 0.00005 wt % to about 5 wt % of a levothyroxine salt;
   (b) at least about 50 wt % of a β-form microcrystalline cellulose particles, said β-form microcrystalline cellulose particles having generally flat needle-shapes, a bulk density in a range of from about 0.10 g/cm$^3$ to about 0.23 g/cm$^3$, and a conductivity of less than about 200 μS/cm; and
   (c) about 0.5 wt % to about 30 wt % disintegrating agent;
wherein (1) at least about 90 wt % of the levothyroxine salt in the composition dissolves in an aqueous solution in less than about 5 minutes, (2) potency loss on average for said levothyroxine salt is no more than about 0.2% per month for a period of at least about 18 months, and (3) said composition is essentially sugar-free.

* * * * *